US012440362B2

(12) United States Patent
Lerner et al.

(10) Patent No.: US 12,440,362 B2
(45) Date of Patent: Oct. 14, 2025

(54) DIFFERENTIAL AND VARIABLE STIFFNESS ORTHOSIS DESIGN WITH ADJUSTMENT METHODS, MONITORING AND INTELLIGENCE

(71) Applicant: Arizona Board of Regents on Behalf of Northern Arizona University, Flagstaff, AZ (US)

(72) Inventors: Zachary F Lerner, Flagstaff, AZ (US); Emmanuella Tagoe, Flagstaff, AZ (US); Chancelor Cuddeback, Flagstaff, AZ (US)

(73) Assignee: ARIZONA BOARD OF REGENTS ON BEHALF OF NORTHERN ARIZONA UNIVERSITY, Flagstaff, AZ (US)

( * ) Notice: Subject to any disclaimer, the term of this patent is extended or adjusted under 35 U.S.C. 154(b) by 271 days.

(21) Appl. No.: 18/233,236

(22) Filed: Aug. 11, 2023

(65) Prior Publication Data

US 2023/0390094 A1 Dec. 7, 2023

Related U.S. Application Data

(63) Continuation-in-part of application No. 18/095,940, filed on Jan. 11, 2023, now Pat. No. 12,127,963,
(Continued)

(51) Int. Cl.
*A61F 5/01* (2006.01)

(52) U.S. Cl.
CPC .... *A61F 5/0127* (2013.01); *A61F 2005/0155* (2013.01); *A61F 2005/0167* (2013.01); *A61F 2005/0179* (2013.01)

(58) Field of Classification Search
CPC .. A61F 2/6607; A61F 2002/5072; A61F 5/01; A61F 5/0102; A61F 5/0113;
(Continued)

(56) References Cited

U.S. PATENT DOCUMENTS

| | | | |
|---|---|---|---|
| 5,058,574 A | 10/1991 | Anderson et al. | |
| 5,458,656 A | 10/1995 | Phillips | |

(Continued)

FOREIGN PATENT DOCUMENTS

| | | | |
|---|---|---|---|
| CN | 106826763 | 6/2017 | |
| CN | 111773038 A * | 10/2020 | ........... A61H 1/0262 |
| WO | 2016067229 A1 | 5/2016 | |

*Primary Examiner* — Tarla R Patel
(74) *Attorney, Agent, or Firm* — Quarles & Brady LLP

(57) ABSTRACT

An assistive ankle foot orthosis is described. The AFO has a vertical shank member arranged laterally to a user's limb. The member carries a rotational bearing and a rotational element such as a pulley. The rotational bearing is lateral to a user's ankle. The pulley is connected to a footplate. The footplate can be actuated to provide joint movement assistance or resistance to the user upon rotation of the pulley. The AFO includes an ankle angle and angular velocity sensor and a pressure sensor located under the user's forefoot. The AFO includes a controller that computes an estimate of the user's peak joint power on the basis of a series of products of measurements of foot pressure and angular velocity.

21 Claims, 21 Drawing Sheets

Related U.S. Application Data which is a continuation of application No. 17/515,300, filed on Oct. 29, 2021, now Pat. No. 12,133,811.

(60) Provisional application No. 63/215,336, filed on Jun. 25, 2021, provisional application No. 63/107,275, filed on Oct. 29, 2020.

(58) Field of Classification Search
CPC ............ A61F 5/0127; A61F 2005/0155; A61F 2005/0179; A61F 2002/5018; A61F 2005/0167; A61F 5/0123; A61F 2005/0169; A61F 2005/0132; A61F 5/0585; A61H 3/00; A61H 1/0266
See application file for complete search history.

(56) References Cited

U.S. PATENT DOCUMENTS

| | | | |
|---|---|---|---|
| 7,578,799 | B2 | 8/2009 | Thorsteinsson et al. |
| 8,075,633 | B2 | 12/2011 | Herr et al. |
| 8,114,034 | B2 | 2/2012 | Ikeuchi et al. |
| 8,267,876 | B2 | 9/2012 | Ashihara et al. |
| 8,419,804 | B2 | 4/2013 | Herr et al. |
| 9,597,217 | B2 | 3/2017 | Patton et al. |
| 9,788,985 | B2 | 10/2017 | Dollar et al. |
| 10,076,462 | B2 | 9/2018 | Johnson et al. |
| 10,179,079 | B2 | 1/2019 | Strausser et al. |
| 10,517,788 | B2 | 12/2019 | Lee et al. |
| 10,561,564 | B2 | 2/2020 | LaChappelle et al. |
| 10,729,610 | B2 | 8/2020 | Matthew et al. |
| 11,110,024 | B2 * | 9/2021 | Yagi ......................... A61H 3/00 |
| 2003/0115031 | A1 | 6/2003 | Dariush et al. |
| 2004/0249316 | A1 | 12/2004 | Ashihara et al. |
| 2005/0059908 | A1 | 3/2005 | Bogert |
| 2005/0097970 | A1 | 5/2005 | Nurse |
| 2007/0027421 | A1 | 2/2007 | Nobbe et al. |
| 2007/0061016 | A1 | 3/2007 | Kuo et al. |
| 2008/0319361 | A1 | 12/2008 | Messer |
| 2010/0063424 | A1 | 3/2010 | Kudoh et al. |
| 2010/0164728 | A1 | 7/2010 | Plost |
| 2011/0028871 | A1 | 2/2011 | Shishido |
| 2011/0213599 | A1 | 9/2011 | Jacobsen et al. |
| 2011/0214524 | A1 | 9/2011 | Jacobsen et al. |
| 2011/0264238 | A1 | 10/2011 | van der Merwe et al. |
| 2011/0295164 | A1 | 12/2011 | Jacobsen et al. |
| 2012/0289870 | A1 | 11/2012 | Hsiao-Wecksler et al. |
| 2012/0293323 | A1 | 11/2012 | Kaib et al. |
| 2012/0330395 | A1 | 12/2012 | Dar et al. |
| 2013/0006159 | A1 | 1/2013 | Nakashima et al. |
| 2013/0053736 | A1 | 2/2013 | Konishi |
| 2013/0158444 | A1 | 6/2013 | Herr et al. |
| 2013/0190669 | A1 * | 7/2013 | Rokosz ................. A61F 5/0125 602/16 |
| 2013/0226048 | A1 | 8/2013 | Unluhisarcikli et al. |
| 2013/0289452 | A1 | 10/2013 | Smith et al. |
| 2014/0100492 | A1 | 4/2014 | Nagasaka |
| 2014/0200491 | A1 | 7/2014 | Julin et al. |
| 2014/0260950 | A1 | 9/2014 | Cook |
| 2015/0321342 | A1 | 11/2015 | Smith et al. |
| 2015/0374573 | A1 | 12/2015 | Horst et al. |
| 2016/0045385 | A1 | 2/2016 | Aguirre-Olliger et al. |
| 2016/0143800 | A1 | 5/2016 | Hyung et al. |
| 2016/0296345 | A1 | 10/2016 | Deshpande et al. |
| 2016/0338857 | A1 * | 11/2016 | Herr ..................... B25J 19/0008 |
| 2017/0119613 | A1 | 5/2017 | Roh et al. |
| 2017/0196751 | A1 | 7/2017 | Smith et al. |
| 2017/0202725 | A1 | 7/2017 | Robertson et al. |
| 2017/0273853 | A1 | 9/2017 | Nagata et al. |
| 2017/0319369 | A1 | 11/2017 | Han et al. |
| 2018/0055711 | A1 | 3/2018 | Choi et al. |
| 2018/0085277 | A1 | 3/2018 | Julin |
| 2018/0085280 | A1 | 3/2018 | Shimada et al. |
| 2018/0092536 | A1 | 4/2018 | Sandler et al. |
| 2018/0116851 | A1 | 5/2018 | Lee |
| 2018/0125738 | A1 | 5/2018 | Witte et al. |
| 2018/0161188 | A1 | 6/2018 | Zistatsis et al. |
| 2018/0168907 | A1 | 6/2018 | Huang et al. |
| 2018/0177672 | A1 | 6/2018 | Uchida et al. |
| 2019/0015286 | A1 | 1/2019 | Glaister et al. |
| 2019/0105215 | A1 | 4/2019 | Dalley et al. |
| 2019/0105777 | A1 | 4/2019 | Dalley et al. |
| 2019/0192373 | A1 | 6/2019 | Vouga et al. |
| 2019/0232485 | A1 | 8/2019 | Reese |
| 2019/0282424 | A1 | 9/2019 | Lerner |
| 2019/0343710 | A1 | 11/2019 | Lemmer |
| 2019/0344433 | A1 | 11/2019 | Lerner |
| 2020/0039061 | A1 | 2/2020 | Sankai |
| 2020/0253773 | A1 | 8/2020 | Logue |
| 2021/0291355 | A1 | 9/2021 | Lerner et al. |
| 2021/0298984 | A1 | 9/2021 | Bulea et al. |
| 2021/0369536 | A1 | 12/2021 | Mooney et al. |
| 2021/0378904 | A1 | 12/2021 | Lerner et al. |
| 2022/0000703 | A1 | 1/2022 | Lerner et al. |
| 2022/0079833 | A1 | 3/2022 | Lerner |
| 2022/0133519 | A1 | 5/2022 | Lerner et al. |

* cited by examiner

DIFFERENTIAL AND VARIABLE STIFFNESS ORTHOSIS DESIGN WITH ADJUSTMENT METHODS, MONITORING AND INTELLIGENCE

CROSS-REFERENCE TO RELATED APPLICATIONS

This application is a continuation-in-part of U.S. application Ser. No. 18/095,940 entitled "Differential and Variable Stiffness Orthosis Design With Adjustment Methods, Monitoring and Intelligence," which is a continuation of U.S. application Ser. No. 17/515,300 entitled "Differential and Variable Stiffness Orthosis Design With Adjustment Methods, Monitoring and Intelligence," filed on Oct. 29, 2021, which claims priority to U.S. Provisional Application 63/107,275 entitled "Differential and Variable Stiffness Orthosis Design With Adjustment Methods, Monitoring and Intelligence," filed on Oct. 29, 2020, and U.S. Provisional Application 63/215,336 entitled "Parallel Elastic Leaf Spring for Cable-Actuated Lower Extremity Exoskeleton," filed on Jun. 25, 2021, the entire contents of which are incorporated in their entirety herein by reference.

STATEMENT CONCERNING FEDERALLY-FUNDED RESEARCH

This invention was made with government support under Grant No. 1R15HD099664 awarded by the National Institutes of Health. The government may have certain rights in the invention.

BACKGROUND

A number of injuries or conditions can lead to disorders that affect muscle control. Individuals with muscle control disorders frequently experience a downward trend of reduced physical activity and worsening of gait function leading to a permanent decline in ambulatory ability. Upper- or lower-extremity orthoses, including ankle foot orthoses (AFOs), are commonly prescribed for individuals who suffer from such muscle control disorders, or other impairments, as from stroke, incomplete spinal cord injury and cerebral palsy. These devices provide mobility enhancement by applying assistive joint torque through the gait cycle. Existing devices use a variety of design approaches to accomplish this fundamental aim. These devices may include Bowden cable actuation, direct-drive shank mounted motors, fabric shank interfaces, bilateral carbon fiber frames, and lateral lower leg structures. Certain devices can also be used for training or strengthening aids, by providing active resistance during some or all phases of the gait cycle.

AFOs generally include footplates to direct torsional force provided at the angle toward the ground, or additionally alternatively, to resist torsional forces imparted by the user's ankle joint. The footplate is located beneath the user's foot, and between the user's foot and the ground, typically on the foot bed of a shoe worn by the user. In addition to constituting a force transmitting interface between the user's foot and the ground, in the case of active devices, the foot plate typically carries one or more sensors, such as pressure sensors, which may measure the force being applied to the foot plate or the ground by the user of the device. Inventive embodiments below describe certain improvements to passive, quasi-passive and active AFOs.

BRIEF SUMMARY

Embodiments of the invention are directed to a passive or active ankle foot orthosis for assisting with ankle motion, training, rehabilitation and the like. The AFO includes an adjustable tensioning component (e.g., one or more springs) coupled to a transmission linkage (e.g., a set of Bowden cables, chain, etc., or a tab), and an extended vertical member coupled to a user's leg via, e.g., a calf cuff. A rotatable bearing is mounted within the member, and is rotatable by a pulley connected to the cables. The bearing is coupled to a footplate, and is rotatable in a plantar direction or a dorsal direction by a wearer. Motion in these directions can be assisted or resisted depending on the tension applied to the cables by the tensioning component. In particular, a tensioning component like a spring can store energy during a portion of the ankle rotation, and then the energy as assistive torque when the rotation is reversed. In certain embodiments, the extended vertical member is a tubular member having a closed, circumferential cross section, and the bearing is located within the interior space defined by the walls or wall of the tubular member. In preferred embodiments, the vertical member is arranged laterally with respect to the user's leg, and the rotational bearing is arranged such that its axis of rotation is coincident with the user's ankle. In preferred embodiments described below, tensioning components allow for active or passive tensioning, and they provide an assistive or resistive torque bias to the footplate coupled to the rotational bearing.

In one aspect, the invention includes a novel joint orthosis design having differential and or variable stiffness via manual, automated, or passive mechanical adjustment.

In one aspect, the invention is directed to a joint orthosis such as an AFO. The AFO includes a modular, laterally-mounted hinged design, which is to say, that the point of rotation of the orthosis is lateral to the user's ankle. The orthosis is comprised of a distal attachment component, an "upright" component that mounts laterally to the joint (for AFO designs), a hinge mechanism located in line with the joint, and a proximal attachment point. The distal attachment component may include a footplate, and the proximal attachment point may include a calf-cuff. The distal and proximal attachment components may be swapped out for difference sizes. The upright may be comprised of a rigid carbon fiber circular, oval, rectangular, hexagonal, square or other polygonal tube. The hinge mechanism may incorporate a pulley or cam placed within the upright tube that rotates relative to tube through bearings or bushings. The lateral upright design allows for modularity of the components, minimizes medially-protruding features that cause contact with other parts of the body, and minimizes anterior or posterior protruding features that may cause contact with objects in the environment.

In another aspect, the AFO includes differential stiffness spring components, for example, linear, compression, rotary, or leaf springs, for the flexion (dorsi extension) and extension (plantar extension) directions. In an assistive configuration, a spring component may be engaged such that the orthosis resists extension during the stance phase and/or resists flexion during the swing phase. In a training configuration, these forces may be reversed. For lower-extremity (e.g., AFO) configurations there may be stance phase spring engagement and/or swing phase spring engagement.

In certain embodiments, AFO's according to the invention exhibit velocity-dependent stiffness. In such embodiments, the orthosis may include a damping mechanism in the flexor or extensor directions to provide automatic velocity-dependent stiffness adjustments. Such embodiments may provide added stiffness when the user is running, for example. Alternative spring configurations are provided for flexion or extension resistance. For lower-extremity embodiments, the orthosis spring components may be configured to provide extension resistance during the stance phase and/or flexion resistance during the swing phase.

AFO's having tensioning springs according to described embodiments have adjustable flexion and extension equilibrium angles, which are the angles at which the flexion or extension spring component becomes engaged. The springs can be configured so that the equilibrium angle is the same or different for the flexion and extension directions.

Similarly, some embodiments allow for quick, manual adjustment to the flexion and extension spring stiffnesses through turning a knob, adjusting a slider, lever, or other similar mechanism, without the need of hand or power tools. In additional embodiments, components or mechanisms are included to adjust the flexion or extension spring stiffnesses based on joint angle, walking terrain, locomotor condition (walking, running) or speed. Spring stiffness could be adjusted by adding or subtracting linear springs in parallel, pre-loading a rotational spring, or adjusting the pivot point on a leaf spring. In some orthoses of the of the aforementioned mechanical designs, components may or may not include a small actuator (e.g., DC motor) to adjust the spring stiffness, equilibrium angle, or assist/resist mode of operation.

In some configurations, mounted within or outside of the upright, the spring components may include linear extension springs, linear compression springs, leaf springs (e.g., an elastic carbon fiber bar), linear, non-linear, or constant force rotary springs.

In certain embodiments, variable stiffness AFO's include a variety of sensors and data processing components usable to determine how to adjust stiffness. In such embodiments, the orthosis includes the necessary electromechanical and software features (e.g., microprocessor, sensors and wireless connectivity, cloud server), making it a connected, intelligent orthosis. By tracking sensor data about the user's ankle position, velocity and acceleration, foot pressure, and the linear and angular acceleration of the AFO itself, such embodiments can provide intelligent recommendations for adjustment of stiffnesses or equilibrium angles. The recommendations may be provided to a user, who may manually adjust the device, or to the user's clinical or rehab team, or the device may automatically adjust the device to improve device function and performance.

In one embodiment, a wearable assistive device is described. The device has an extended, tubular structural member having a closed circumferential cross section, a first end and a second end defining a long axis through a center of the extended structural member. The device includes an attachment device coupled to the member and extending medially from the member, the attachment device configured to secure the member to a limb of a user. The device also has a rotational bearing disposed within the extended structural member and positioned on the long axis near the second end of the extended structural member. The device includes a pulley coupled to the rotational bearing, and a footplate dimensioned to support a foot of a wearer of the assistive device and coupled to the pulley such that it may rotate with respect to the long axis of the extended tubular member. The device also has a first cable having a first end and a second end, the first end coupled to a first spring, the second end coupled to the pulley.

Another embodiment is directed to an alternative wearable assistive device. The device has an extended, hollow, tubular structural member having a closed circumferential cross section, a first end and a second end defining a long axis through a center of the extended structural member. The device also has an attachment device coupled to the member and extending medially from the member, the attachment device configured to secure the member to a limb of a user. There is a rotational bearing disposed within the extended structural member and positioned on the long axis near the second end of the extended structural member, and a rotational element coupled to the rotational bearing. The device includes a footplate dimensioned to support a foot of a wearer of the assistive device and coupled to the rotational element such that it may rotate with respect to the long axis of the extended tubular member. The device also includes a leaf spring arranged within the hollow, tubular member, and a cable having a first end and a second end, the first end coupled to the leaf spring and the second end coupled to the rotational element.

In one embodiment, an exoskeleton device is disclosed. The device includes a shank and a footplate rotatably coupled to the shank via a rotational bearing. The device further includes an angle sensor configured to measure an angle between the shank and the footplate and the velocity of the angular change between the shank and the footplate, and a pressure sensor at the footplate configured to measure pressure exerted by a user's foot. The device also includes an integral or remote feedback modality. The device also includes an integral or remote controller including a microprocessor in communication with the angle sensor and the pressure sensor. The controller is configured to compute an estimate of joint ankle power developed by the user during stance phase while walking, and to activate the feedback modality based on a comparison of the estimate of peak joint ankle power and a predetermined metric. The angle sensor may be one of an angle encoder, an inertial measurement unit and an array of positional sensors.

In another embodiment, the controller is configured to compute the estimate of joint ankle power by estimating peak joint ankle power by computing a series of products of measurements of user ankle angular velocity and user foot pressure taken during stance phase while the user walks, and computing an estimate of peak joint ankle power on the basis of the series of products. In some embodiments, computing the estimate of peak joint ankle power on the basis of the series of products comprises selecting a peak product of the series.

In another embodiment, computing the estimate of joint ankle power comprises computing a series of products of measurements of user ankle angular velocity and user foot pressure taken during stance phase while the user walks and computing the average of the products or integrating across the products.

In certain embodiments, the device includes a transceiver configured to wirelessly transmit sensor data to the controller, and wherein the controller is located in a computing device remote from the shank and footplate.

In an embodiment, the controller activates the feedback modality in a first state to indicate compliance with the performance metric and a second state to indicate non-compliance with the performance metric.

In some embodiments, the performance metric is based on an average of historical peak products of measurements taken by the angle and pressure sensors during stance phase while the user walks.

In certain embodiments, the feedback modality is housed in a device remote from shank and footplate. In some embodiments, the feedback modality comprises an LED array configured to provide color-coded visual feedback and/or a speaker, and/or a vibrotactile interface that is positioned to supply vibrotactile feedback to the calf of a user of the device, and/or a visual display on a handheld device, and/or a speaker on a handheld device.

In some embodiments, the device includes a control unit having at least one actuator and a transmission assembly operably coupling the actuator to the hinged assembly and configured to rotate the footplate with respect to the shank. In such embodiments, the controller is configured to cause the actuator to rotate the footplate with respect to the shank based on the comparison of the estimate of peak joint ankle power and a predetermined metric. In some embodiments, the controller is configured to rotate the footplate in a direction of foot extension based on non-compliance with the performance metric.

In certain embodiments, the sensors are in electronic communication with the controller via a wireless transceiver, and the controller including the microprocessor is housed in one of a smart phone, tablet or personal computer. In some embodiments, the controller including the microprocessor is housed in a portable electronic device, which is configured to provide the feedback modality. In certain cases, the controller including the microprocessor is housed proximate to the shank and hinged assembly. For some cases, the feedback modality is configured as a scoring system based on collecting rewards based on repeated compliance with the performance metric.

In certain embodiments, the device is a passive device and may include a carbon fiber leaf spring configured to provide adjustable assistance or resistance to the user's ankle plantar flexion or dorsi flexion during walking. In cases where the device is active, the transmission assembly may include a pair of Bowden cables and a pulley coupled to the bearing.

AFOs according to inventive embodiments have certain advantages, which are also applicable to assistive orthoses for other joints. For example, the embodiments described below improve the ability of an individual to fit a device and perform self-calibration or customization of the amount and angle of joint support (i.e., stiffness) without the need to visit a certified orthoptist. The self-adjustability of the device permits a user to dial-in different support quantities or change the angle as the user progresses throughout a rehabilitation program, or encounters different sorts of walking terrain (i.e., flat areas versus hilly areas). Additionally, inventive embodiments accommodate interchangeable components (e.g., springs, vertical members or footplates) that can be swapped out for larger/smaller sizes. Inventive embodiments provide the option for user and device monitoring and are usable to create a connected device that can be used for telerehab or telemedicine. Additionally, the device modifications described herein are usable to optimize performance across different ambulatory conditions. Additional advantageous will become clear upon consideration of the detailed description of the preferred embodiments taken in conjunction with the accompanying drawings.

BRIEF DESCRIPTION OF THE DRAWINGS

The drawings described herein constitute part of this specification and includes exemplary embodiments of the present invention which may be embodied in various forms. It is to be understood that in some instances, various aspects of the invention may be shown exaggerated or enlarged to facilitate an understanding of the invention. Therefore, drawings may not be to scale.

DETAILED DESCRIPTION OF THE PREFERRED EMBODIMENTS

The described features, advantages, and characteristics may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment. References to "users" refer generally to individuals accessing a particular computing device or resource, to an external computing device accessing a particular computing device or resource, or to various processes executing in any combination of hardware, software, or firmware that access a particular computing device or resource. Similarly, references to a "server" refer generally to a computing device acting as a server, or processes executing in any combination of hardware, software, or firmware that access control access to a particular computing device or resource.

Figure 1:
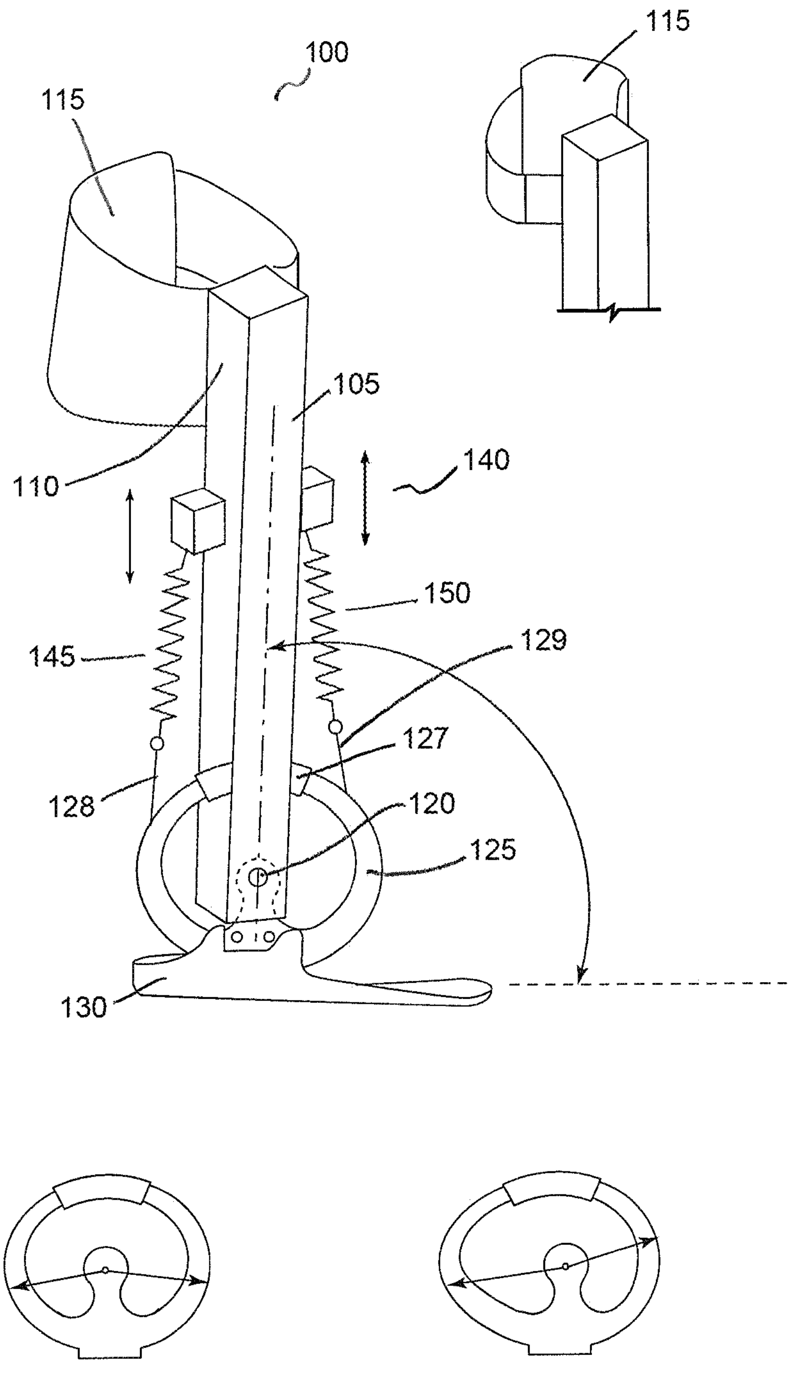
FIG. 1 depicts one embodiment of a novel ankle foot orthosis with interchangeable components, and differential and variable spring stiffness (top). Potential ankle pulley component designs (bottom).

For purposes of description herein, the terms "upper," "lower," "right," "left," "rear," "front," "vertical,", "upright", "horizontal," and derivatives thereof shall relate to the embodiment of the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary examples of the inventive concepts defined in the appended claims. Hence, specific dimensions and other physical characteristics relating to the examples disclosed herein are not to be considered as limiting, unless the claims expressly state otherwise.

As required, detailed examples of the present invention are disclosed herein. However, it is to be understood that the disclosed examples are merely exemplary of the invention that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present invention.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

As used herein, the term "and/or," when used in a list of two or more items, means that any one of the listed items can be employed by itself, or any combination of two or more of the listed items can be employed. For example, if any assembly or composition is described as containing components A, B, and/or C, the assembly or composition can contain A alone; B alone; C alone; A and B in combination; A and C in combination; B and C in combination; or A, B, and C in combination.

As used herein, the terms "assistance" and "resistance" may be used interchangeably to signify the direction of external torque applied to a joint that may be perceived as augmenting (making a movement easier, assistance) or harder (resistance).

The following disclosure relates to an AFO comprised of a footplate component, an "upright" component that mounts laterally to the lower limb, a hinge mechanism located in line with the ankle joint, and a calf attachment point. The footplate is interchangeable and can be swapped out for different sizes. The calf attachment component could be a "calf cuff" or "shin cuff" that incorporates a rigid or semi-rigid shell with a soft (e.g., foam) lining; the calf attachment can be adjust up or down the limb and be interchanged for different sizes. The upright may be comprised of a rigid carbon fiber circular, oval, rectangular, hexagonal, square or other polygonal tube. The hinge mechanism may incorporate a pulley, cam, sprocket or a combination of these placed within the upright tube that rotates relative to upright through bearings or bushings. The lateral upright design, quick release features and component modularity of the design allows the AFO to grow with a child. In some configurations, mounted within or outside of the upright, the spring components may include linear extension springs, linear compression springs, leaf springs (e.g., elastic carbon fiber bar), linear, non-linear, or constant force rotary springs. A clutch or engaging/disengaging ratchet may be used to differentially adjust spring timing.

The AFO may include different joint stiffness components (e.g., a linear, compression, rotary, or leaf spring) for the plantar-flexion direction (pointing toes downward) and the dorsi-flexor direction (pointing toes upward), so that the plantar-flexor direction is stiffer than the dorsi-flexor direction. In an assistive configuration, a spring component may be engaged such that the AFO resists extension during the stance phase and/or resists flexion during the swing phase. In a resistive configuration, a spring component may be engaged such that the AFO resists plantar-flexion during the stance phase and/or resists dorsi-flexor during the swing phase. The AFO may have adjustable plantar-flexor and dorsi-flexor equilibrium angles.

In one embodiment of a quasi-passive novel AFO, a small DC motor actuates a mechanism to adjust the equilibrium angles and/or spring stiffnesses in the plantar- and/or dorsi-flexor directions. In another configuration, the AFO may include knobs, levers, or sliders to easily customize and adjust plantar- or dorsi-flexor spring function.

In one embodiment, the intelligent AFO tracks user and device function, automates recommendations for device settings, performs adjustments or instructs the user how to make adjustments. The device streams use and compliance information to a cloud-based server for monitoring by the clinician and insurance company.

Referring now to FIG. 1, there is shown a schematic diagram of a variable tension AFO according to an inventive embodiment. In the embodiment of FIG. 1 an AFO 100 includes a rigid upright member 105. Member 105 is preferably a hollow tubular member formed of carbon fiber or the like, having a square, rectangular, other polygonal, circular or elliptical cross section. Member 105 may have a constant or variable cross section throughout its length. Member 105 includes at a proximal end a first attachment point 110, which receives an attachment device 115 such as a calf cuff. Attachment device 115 may alternatively be a shin cuff (pictured at right), or may be an attachment device capable of securing AFO 100 to some other limb or some other portion of the leg. In a preferred embodiment, attachment device 115 is attached to member 105 by a rigid but detachable mechanism, such as fasteners that secure device 115 to member 105 through non-illustrated fastener holes. Thus, attachment device 115 is replaceable, such that the AFO may be configured for users having legs of different sizes. In one embodiment, attachment device 115 may be attached at a plurality of positions along the proximal area of member 105 to allow for adjustment of the distance between attachment device 115 and rotational bearing 120. Adjusting the position of cuff 115 with respect to rotational bearing 120 allows the user to mount AFO to the user's leg such that rotational bearing is preferably positioned such that its rotational axis is through the user's ankle. In a preferred embodiment, when worn, the member 105 of the AFO is located on the lateral side of a user's leg, and device 115 is oriented on member 105 to engage with the leg of the user to position member 105 on a medial side of the user's leg. That is to say, device 115 may extends medially from member 105.

AFO 100 also includes a rotational bearing 120, which engages with a pulley, cam, sprocket or some other rotational hinge element 125 such that rotational hinge element 125 is secured to and may rotate with respect to member 105. Preferably, the member 105 has a long axis that passes through and is perpendicular to an axis of rotation of bearing 120. In one embodiment rotational element 125 is a circular pulley that is mounted to rotational bearing 120 such that its lateral and medial sides are both located within the perimeter walls of the member 105. In such cases, member 105 may include one or more apertures (130) allowing passage of a portion of the pulley sheave through the member 105. Additionally, pulley 125 may include a component 127 of its sheave to selectively render the perimeter of the sheave discontinuous so as to facilitate installation of the pulley 125 into member 105 before it is secured to bearing 120. Component 127 may be, for example, a removable portion of the sheave, or a translating or swinging gate that opens a gap in the sheave. In the illustrated arrangement, the rotational bearing, and therefore the pulley, is supported on both ends by walls of the tubular member 105, which preferably is made of a stiff material like carbon fiber. This gives the pulley bilateral support, which is useful to prevent out of plane deflection of the pulley when the pulley is being actuated by cables, from either the passive spring components, or when used with active drive cables. Co-pending, co-owned U.S. patent application Ser. No. 17/343,628 entitled "Cable-Actuated, Kinetically-Balanced, Parallel Torque Transfer Exoskeleton Joint Actuator With Or Without Strain Sensing," describes acceptable, exemplary configurations of AFOs having vertical members and pulleys which are usable in conjunction with embodiments described herein. That reference is incorporated herein in its entirety.

The AFO 100 of FIG. 1 also includes a footplate or insole bracket 130 attached to rotational element 125. The footplate 130 extends medially, and is configured and arranged to engage with the bottom of a user's foot when the AFO is worn. Footplate 130 may provide rotational force (i.e., torque) to a user's foot, tending to assist or resist ankle flexion or extension, when torque is applied to pulley 125. Footplate 130 is detachable from pulley 125, e.g., by one or more fasteners, such that it may be replaced in the event of wear or the desire to change the footplate's size or shape. Acceptable footplate configurations usable with the embodiments described herein are described in co-pending, co-owned U.S. patent application Ser. No. 17/365,768 entitled "Optimized Ankle Exoskeleton Foot Plate Function and Geometry," the entirety of which is incorporated herein by reference.

AFO 100 includes a bias and tensioning mechanism, 140, which provides assistive or resistive torque to pulley 125 within certain ranges of rotation of footplate 130. In the embodiment of FIG. 1, one or more linear springs (145, 150) are provided that engage a first side and a second side of the sheave of pulley 125 via cables (128, 129), cord, ribbon, chain or some other tensile force transmission mechanism. As can be seen, spring 145, depending on its vertical position and configuration, will tend to provide extending torque to footplate 130 (i.e., to cause plantar extension or resist flexion/dorsi extension), and spring 150, will tend to provide flexion torque to footplate 130 (i.e., to cause dorsi extension and resist plantar extension). Thus, in an assistive configuration, the AFO of FIG. 1 includes at least one spring component that may be engaged such that the orthosis resists extension during the stance phase and/or resists flexion during the swing phase. Providing a pair of springs enables a stance phase spring engagement and a swing phase spring engagement.

Springs 145, 150 are mounted to member 105 at one of a plurality of attachment points along the front or back (i.e., anterior or posterior) surfaces of the member 105. The provision of a plurality of vertically spaced apart attachment points permit the springs to be biased such that the torsional force provided to the pulley 125 may be varied, both in terms of magnitude, and in terms of setting the pulley's equilibrium position for each spring. Some exemplary arrangements along these lines will now be described.

One function of the arrangement of springs 145, 150 is to set the equilibrium position of footplate 130. The equilibrium position of footplate 130 is the position (i.e., the rotational state) of the footplate when it is not being acted on by external spring forces (other than the forces inherent in non-spring portions of the AFO itself, that is, the friction of the rotational bearing, and gravity acting on the footplate, etc.). The footplate will be in its equilibrium position when the AFO device is, for example, suspended, as in when it is held by the upright member. In one embodiment, when the footplate is in its equilibrium position, the spring forces acting on the pulley are equal and balanced, and the ankle of a user wearing the AFO will receive no extension or flexion assistive or resistive force when the footplate is in the equilibrium position. The positions (along the upright member), and the spring strength (e.g., the spring constant of each spring) may chosen to set the equilibrium position of the footplate at any angle achievable by the physical constraints of the AFO. For example, if both springs equal, and both are anchored to the same position along the upright member, and at equal complimentary positions along the pulley sheaf, the force that each spring exerts on the pulley will be equal. This will be the case regardless of whether or the extent to which the springs are extended, because the degree of each spring's extension will be equal. This arrangement will balance the rotational forces acting on the pulley when the footed is in a horizontal orientation, as shown in FIG. 1. Again, a user wearing the device when the footplate is in this position (i.e., the standing during the stance stage of the gait) will experience no auxiliary torque.

In another aspect, the AFO has adjustable flexion and extension equilibrium angles (i.e., a different footplate equilibrium position for each direction of rotation, set by each spring). Here, the equilibrium angles are the pulley angles or rotation positions at which the flexion or extension spring components become engaged. Referring again to FIG. 1, both springs are associated with the same 0 degree equilibrium angle, and the first spring 145 is engaged upon flexion from 0 degrees, and the second spring 150 is engaged upon extension from zero degrees.

Referring still to the operation of the FIG. 1 embodiment, as set forth above, there is no assistance provided in the stance phase. As the user transitions through mid-stance to toe-off, the shank rotates forward, the heel comes up, and the foot rocks forward over the toes. In the AFO of FIG. 1, during this movement, spring 150 will elongate and exert flexion torque on the footplate, tending to return it to equilibrium position. Such force may be useful to provide flexion assistance to a user's foot as it comes off the ground, as to return it to a level position. Such torque may also be helpful as a training aide—to force the user to push the foot down with more force to complete the movement prior to toe-off. Similarly, spring 145 may exert extension assistive force tending to return the footplate to equilibrium when the user is rotating the footplate up or dorsally. Such force may be helpful in rotating the foot to horizontal after the heel strike phase of the gait. Such force may also be useful as a training aid—to force the user to rotate the foot up with more force prior to heel-strike. By adjusting the spring weight, the user can vary the amount of resistance and assistance provided. By adjusting the spring positions, the user can change the equilibrium point, and therefore, can vary the points in the gait cycle where resistance and assistance are provided.

Additionally, as will be explained below in reference to FIG. 2, by adjusting the positions of the springs, and the equilibrium points of the springs, the user can create a non-linear stiffening or softening response to the resistance/assistance. This is accomplished by shifting the relative equilibrium points of the springs such that they overlap, meaning that one spring will be counteracting the effect of the other spring during at least some portion of the movement.

In alternative embodiments, the orthosis may have a clutch or engaging/disengaging ratchet mechanism on either the flexion spring component or the extension spring component such that it engages or disengages at different angles.

As noted above, the rotational hinge element may take a number of acceptable forms. In some configurations, the hinge mechanism may be a circular pulley (constant radius) or cam pulley (non-constant radius) such that the radius may or may not be constant on the flexion or extension rotational directions. In one embodiment, the variation of radius with angle is different on one side of the pulley versus the other side (such that the sheave does not have symmetry about its centerline). A cam pulley allows for adjustments to joint stiffness as a function of the ankle joint angle. In some configurations, the hinge mechanism may be a toothed-sprocket that engages other sprockets. The main hinge component may be comprised of two separate sprockets, one to engage a flexion sprocket and another to engage an extension sprocket. The secondary sprockets would directly or indirectly apply a resistive or assistive spring force or torque to the main sprocket/hinge mechanism.

Figure 2:
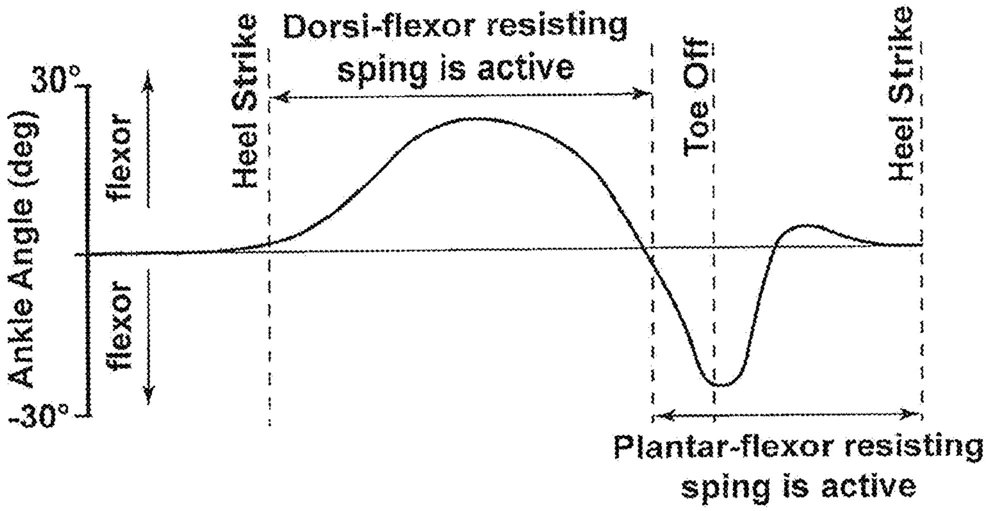
FIG. 2 depicts equilibrium angle and potential linear, stiffening, or softening spring force responses.
Figure 2:
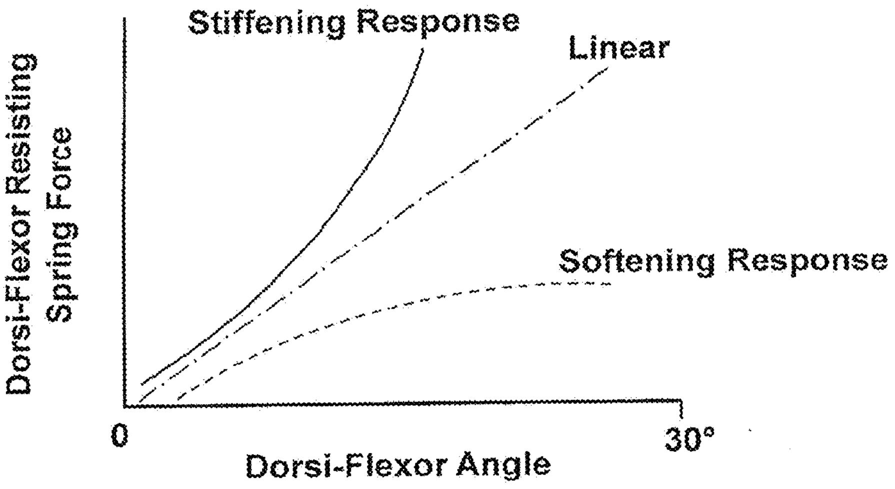

FIG. 2 shows an example of the application of torsional force by the AFO as shown in FIG. 1 having a 0 degree equilibrium position (i.e., a level footplate). As can be seen, at heel strike, the foot is rotated up, in dorsi extension (referred to above as flexion). In this position, spring 145 is in tension, making the device rotationally stiff, and exerting a counter rotational force in the plantar direction. As the foot rocks forward to the 0 degree equilibrium position, the assistive force is zero. As the foot continues to rock forward toward toe-off, spring 150 is in tension, again making the device rotationally stiff, and exerting a counter rotational force in the dorsal direction. After toe off, the foot again transitions to level (and a zero assistance equilibrium position) before preparation for the next heel strike.

It will be appreciated that by choosing different spring strengths, the magnitude of the dorsi and plantar resisting forces relative to one another can be changed. Additionally, for any pair of spring weights, the equilibrium points can be changed by adjusting the positions of the springs. As is shown at the bottom of FIG. 2 the net torque provided to the footplate by the springs can be stiffened or softened throughout the movement by adjusting the positions of the springs. To take one example, suppose that in the 0 degree position shown in FIG. 1, both springs 145, 150 are under tension, but balanced. In this hypothetical, the equilibrium points for the individual springs would be different, but would be equally disposed on either side of a midline of the pulley, such that both springs are exerting equal and opposite force when the footplate is level. As the user moves from stance to toe-off, the user experiences increasing resistance to plantar extension from the elongation of spring 150, and at the same time, decreasing assistance from spring 145 as it compresses. Thus, the resistance (and therefore the assistance that will be provided to return the foot to level after toe-off), increases with the angle of the movement. The same would be true in the opposite direction. During dorsi extension (called dorsi-flexion in FIG. 2), which is rotating the foot up in preparation for heel strike, spring 145 provides resistance as the foot it rotated up from equilibrium. At the same time, spring 150 compresses and provides less assistance. This stiffening response is reflected in the "stiffening response" curve in FIG. 2. A softening response throughout the movement can be achieved by changing the relative equilibrium angles associated with the springs, such that the assistive spring becomes engaged, for example, at larger angles.

Figure 3:
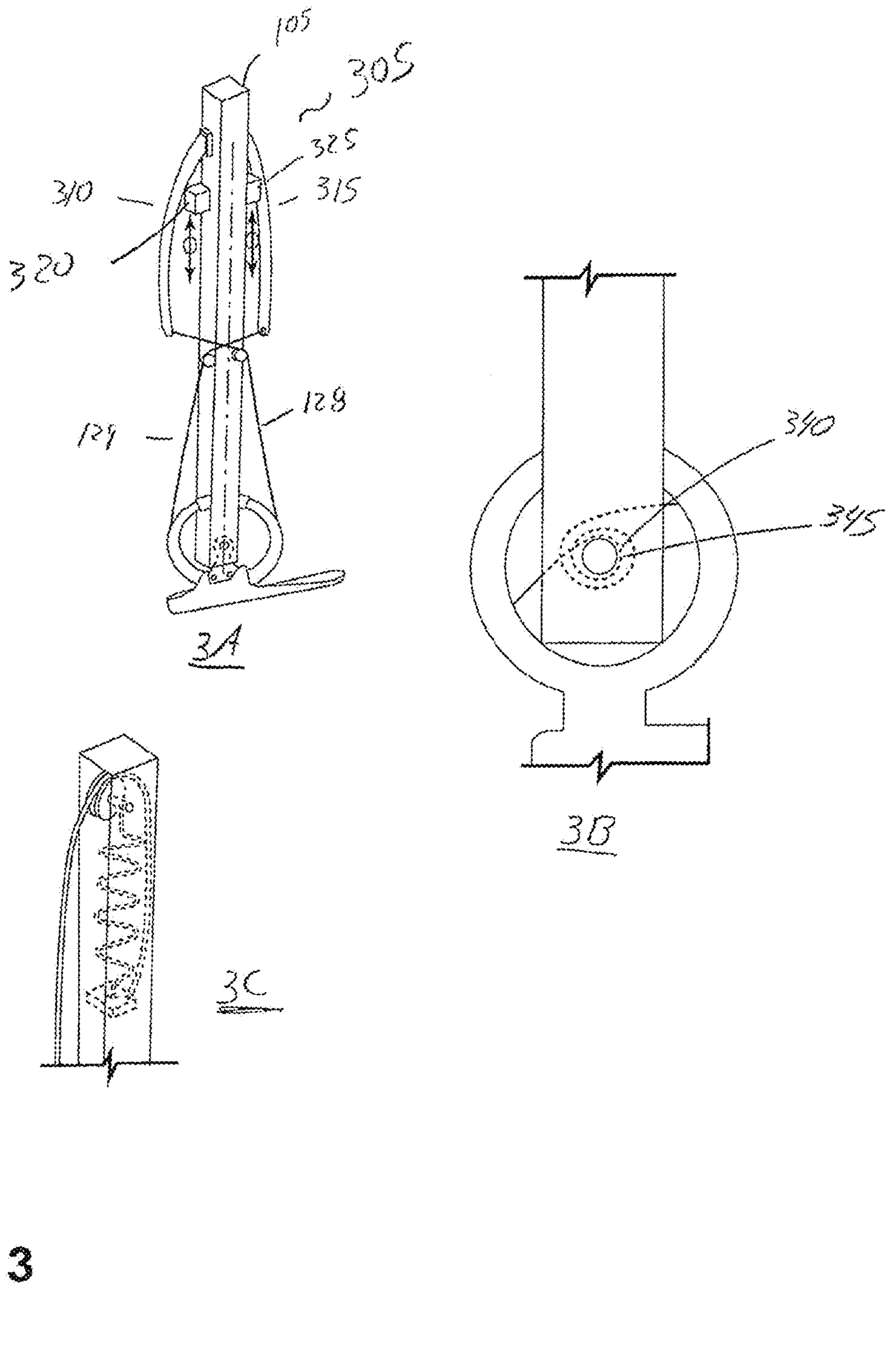
FIG. 3 depicts different spring designs: leaf (3A), internal compression (3C), and rotary (3B).

Alternative arrangements using different sorts of tensioning mechanisms are depicted schematically at FIG. 3. FIG. 3A shows a first alternative AFO 305. In AFO 305, a pair of vertically mounted leaf springs 310, 315 are arranged on a front and back side of member 105. Springs 310, 315 ride on respective pivots 320, 325. Pivots 320, 325 may be fixed, but preferably are slidingly attached to the front and back sides of member 105, for example, in a vertically arranged track, by a rack-and-pinion arrangement, or the like. In such arrangements, pivots may be slid vertically along member 105 and fixed in place. In alternative embodiments, pivots 320, 325 are attachable to member 105 at a variety of discrete or a continuum of fixed positions, by fasteners or the like. Preferably, pivots 320, 325 are independently adjustable. In certain embodiments, pivots 320, 325 are rollers or domes, preferably of some low friction material like polymer. Pivots 320, 325 may be manually adjustable, or translatable by some motorized means. As pivots 320, 325 are translated upward along member 105 toward the fixed connection between springs 310, 315 and member 105, the springs deflect outward from the member, and the free length of the springs shortens, which increases the spring strength. It is contemplated that these various effects will be achieved by the user (or the user's clinical team) by varying the vertical mounting points of the springs, where preferably, the springs themselves (i.e., the spring weights) remain constant. That is to say, this adjustability is accomplished without changing out springs.

Distal ends of springs 310, 315 are connected to tensile force transmitting means 128, 129 (e.g., a cable or chain), via pulleys arranged on or in member 105, to exert pulling force on pulley 125. The cables are routed to engage the distal ends of their respective leaf springs at close to 90 degrees, and preferably, are routed through member 105 (through apertures) to engage pulley 125 on the opposite side. Routing pulleys, as shown, may be provided to accomplish this cable routing. In certain embodiments, routing pulleys are mounted on rotational bearings arranged in the front and back walls of member 105.

FIG. 3B schematically illustrates an alternative embodiment in which a pair of rotary springs 340, 345, are provided that provide counter rotational force at the pulley 125. In cases such as that of FIG. 3B, the rotational springs 340, 345 may be mounted internal to member 105 and medially and laterally on the rotational bearing, for example, on either side of pulley 125. A reinforced ledge or other stopping structure may be provided on the interior of member 105 for the rotational springs to push against as they are loaded. In certain alternative embodiments, this stop may be rotatable, and in some cases, ratcheting, to preload each spring and to change the equilibrium angle associated with each spring. Alternatively, the springs themselves may be rotated with respect to fixed stops.

In an alternative embodiment of FIG. 3B, there is a single rotary spring that is compressed by angular motion in a first direction and extended by angular motion in a second direction. In such cases, there may be one or more adjustable stop surfaces that determine the angle at which the spring starts compressing and the angle at which it starts extending.

FIG. 3C schematically illustrates yet another alternative arrangement using one of more springs that is loaded in compression. The compression spring arrangement of FIG. 3C has the advantage that a single spring may be used, where the spring is connected to both force transmission cables 126, 127, such that compression of the spring provides counter-rotational assistance as the footplate is rotated in either direction. In alternative embodiment, a second spring, which may be a compression spring, is provided for rotation in the other direction.

Combinations of one or more of the spring arrangements depicted in FIGS. 1 and 3 are contemplated and within the scope of the invention.

Figure 4:
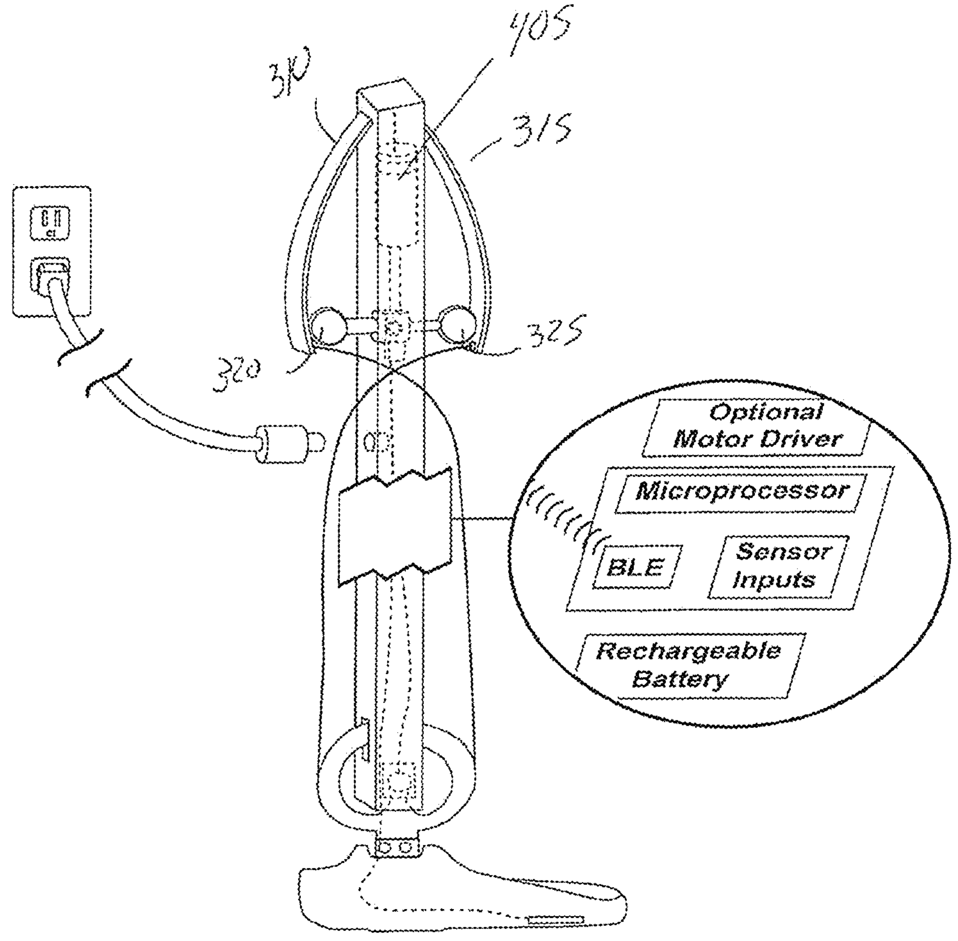
FIG. 4 depicts intelligent AFO components (microprocessor, battery, connectivity, sensors) and optional DC motor for adjusting leaf spring stiffness.

FIG. 4 schematically depicts an alternative embodiment of an AFO according to the invention. The embodiment of FIG. 4 is similar to the embodiment of FIG. 3A in that it uses vertically mounted leaf springs (310, 315) and adjustable pivots (320, 325). However, in the example of FIG. 4, a drive mechanism 405 is provided which can translate the pivots 320, 325 vertically along member 105, thereby adjusting the leaf spring tension, and the amount of torque delivered to the pulley. Such an arrangement is useful for allowing the user to choose the level of stiffness that the AFO provides. In one aspect, drive mechanism includes an actuator such as a DC motor that drives a ball screw in a first or second direction, thereby translating a ball nut. The ball nut is connected by lateral projections to the pivots 320, 325. The lateral projections pass through slots in the front and back surfaces of member 105, and the ball nut may be prevented from rotating with the screw by contact between the lateral projections and the slot's perimeter. Thus, as the screw rotates the ball nut, and therefore the pivots, translate up and down. Other drive mechanisms capable of reversible linear translation are possible, such as cable and pulley, chain and sprocket or rack and pinion arrangements.

In alternative embodiments, each pivot 320, 325 is independently vertically translatable, either manually or through one or more of the drive mechanisms mentioned above. In the case of a mechanized system, this may be accomplished by providing two separate motors. Alternatively, in cases where dynamic or real time adjustability is not a concern, the mechanism that transmits force from the motor to each pivot may be selectable, such that it can selectively translate one pivot, then another. As is discussed above in relation to FIG. 3, having independently adjustable pivots allows the tension being supplied to the pulley by the springs be independently adjustable. This allows the resistance during toe-up and toe-down movements to be independently set.

Drive mechanism 405 may be in electronic communication with drive electronics, which are also shown in FIG. 4. Drive electronics may include a motor driver, which receives control signals from a manual switch or a microprocessor/microcontroller. Motor driver may be powered by a rechargeable battery. Drive electronics may also include a microprocessor or microcontroller in communication with a data transceiver, such as a WiFi or Bluetooth or BLE transceiver. Microprocessor/microcontroller may also be in communication with one or sensors. Sensors may include one or more sensors that provide data on the angular position of the pulley, for example, Hall Effect sensors, IMU, angle encoders or potentiometers. Additional sensors may include accelerometers and gyroscopic or other sensors for detecting angular acceleration. Such sensors may be arranged to gather data regarding the acceleration of the AFO as a whole, for example, to determine its position in the gait cycle. Specifically, such sensors may detect heel strike (from rapid deceleration of the AFO) or swing. Such sensors may be usable to determine whether the user is walking or running, for example, based on the magnitude of the detected accelerations or the frequency of sensed heel strikes. Sensors may also include a pressure sensor, like a force sensitive resistor, located on the footplate under the distal portion of a user's foot, which may gather data reflecting the pressure being exerted by the user on the footplate.

Figure 5:
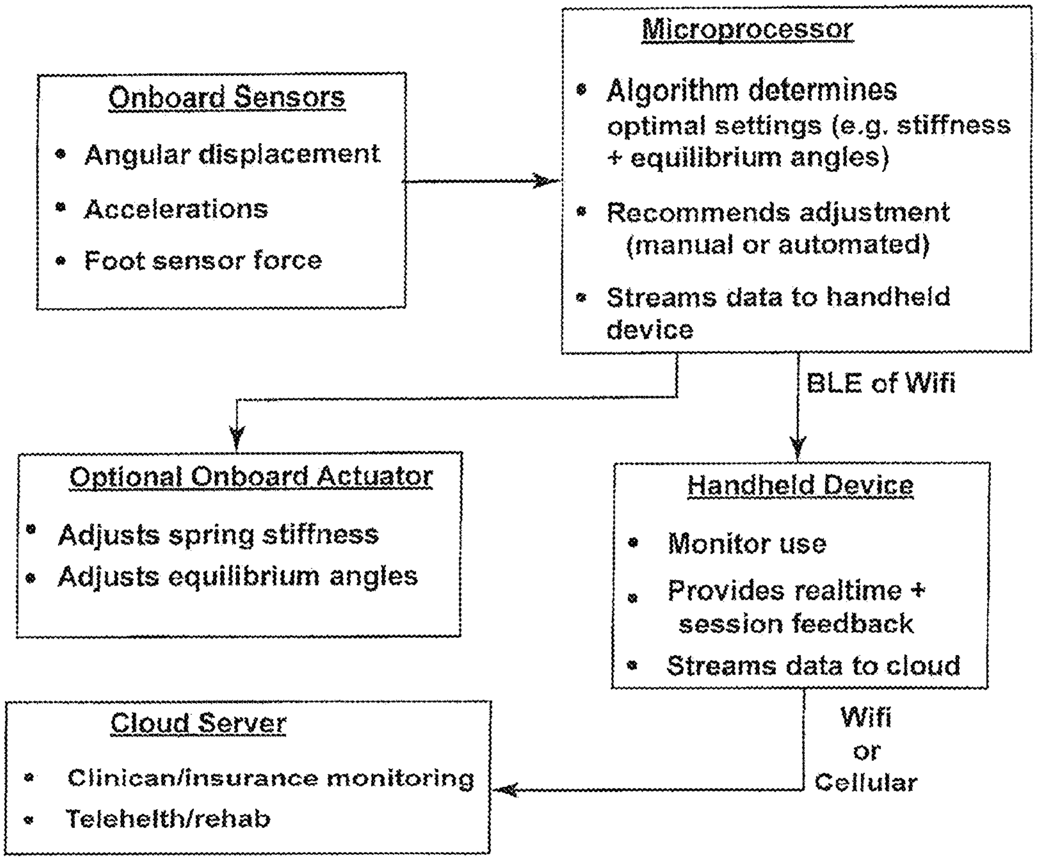
FIG. 5 is schematic depiction of data flow for an intelligent AFO design.

FIG. 5 is a data flow diagram showing, schematically, the operation of the electronic system described above. Onboard sensors may collect use data, which may include data relating to foot pressure, angular displacement of the pulley and/or footplate, and/or angular velocity and acceleration of the pulley or footplate. Additionally, various accelerations may be measured, for example, the angular or linear acceleration of the member 105 or some other part of the AFO. Sensor data is provided to an onboard microprocessor, which analyzes and processes the provided data to generate data about the performance of the device and the activity of the user. For example, the intelligent orthosis system described here may track the number of movements the user performs in a session or over time. For lower-extremity embodiments, the device may track the number of steps, user walking speed, or joint angles. The device may also record and report performance for rehabilitation progress tracking. The microprocessor may also receive the provided data and determine settings, such as spring stiffness and equilibrium angle, on the basis of the received data.

The device may transmit information external to the device (e.g., to the user) regarding the determined spring stiffness and equilibrium settings, so that the user can perform a user-directed manual or motorized adjustment. Alternatively, a microcontroller can provide control signal to the actuator, which adjusts the pivots in accordance with the determined settings. Alternatively or additionally, the determined settings and/or the raw or processed sensor data can be communicated through the transceiver to external computing device such as a handheld device (in the possession or a user, or member of the user's medical or training team), or a remote server such as a cloud server. Either or both of these external computing devices may do the analysis of the data and determination of the spring settings that is discussed above, rather than the onboard microprocessor. In the case where the orthosis is monitored via handheld device (smart phone or tablet), the device may encourage use, provide cues, or use gamification techniques. Either or both of the handheld or cloud server devices may transmit adjustment commands to the microprocessor. As an alternative to direct communication (e.g., over WiFi) between the microprocessor and the cloud server, the handheld device may communicate data to the cloud server, acting as a conduit between the AFO and the cloud server.

For quasi-powered and intelligent configurations as described above, the onboard microprocessor or a remote, connected device, may instruct the onboard actuator(s) to adjust the stiffnesses or equilibrium angles of the spring components. The onboard actuator(s) would then perform the adjustment. The adjustments would be based on a computer algorithm that determines the optimal stiffnesses or equilibrium angles for a given ambulatory condition or speed (e.g., incline, decline, stairs, slow, fast, walking running) based on a foot sensor, angle sensor, accelerometer, or inclinometer in isolation or in combination.

Figure 6:
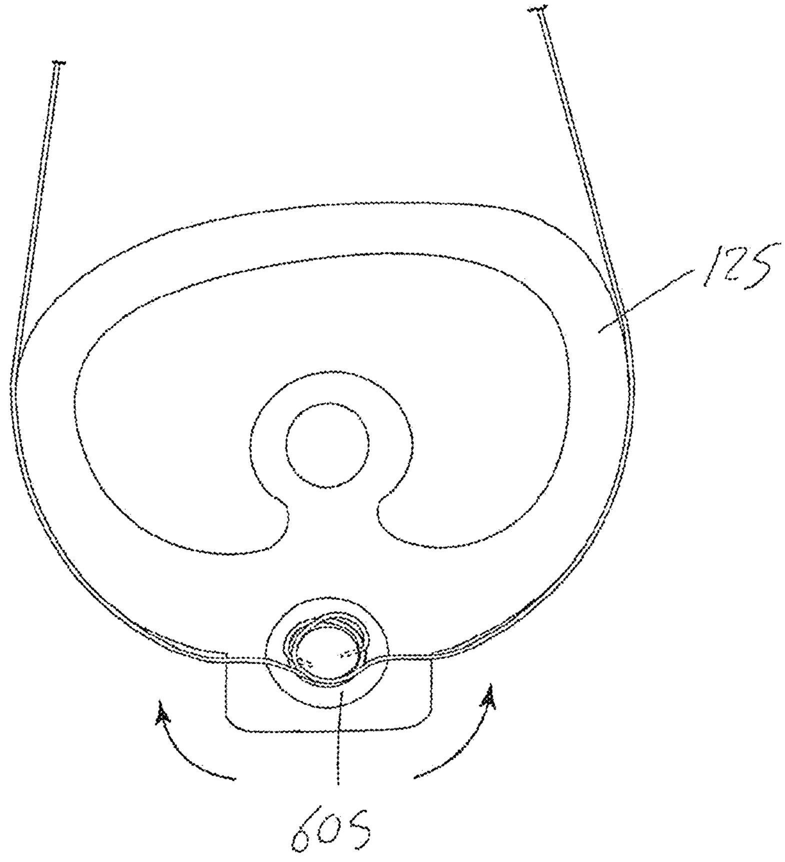
FIG. 6 depicts a manual adjustment knob mounted to the main hinge pulley that adjusts equilibrium angle.

In embodiments, the AFO includes features allowing for quick, manual adjustment (or fine tuning) to the flexion and extension equilibrium angle through turning a knob, adjusting a slider, lever, or other similar mechanism, without the need of hand or power tools. In one example configuration, turning a knob in one direction would tension the cable that attaches to the flexion-resisting spring at the same time, and by the same amount, as loosening the tension to the cable that attaches to the extension-resisting spring; turning the knob in the other direction would have the opposite effect. FIG. 6, for example, shows a pulley 125 having a knob, hub, barrel or sprocket 605, which is selectably rotatable and then rotationally fixable with respect to pulley 125. Distal ends of the transmitting means (e.g., cables) are wound around the knob in opposite directions, and fixed to knob 605. Rotation of the knob creates slack in one cable, while increasing the tension in the other cable. This allows for easy adjustment of the equilibrium angle of the footplate attached to the pulley 125. In certain alternative embodiments, a pair of knobs are provided, around each of which is would one of the cables. In such embodiments, the slack or each cable can be adjusted independently.

Figure 7A:
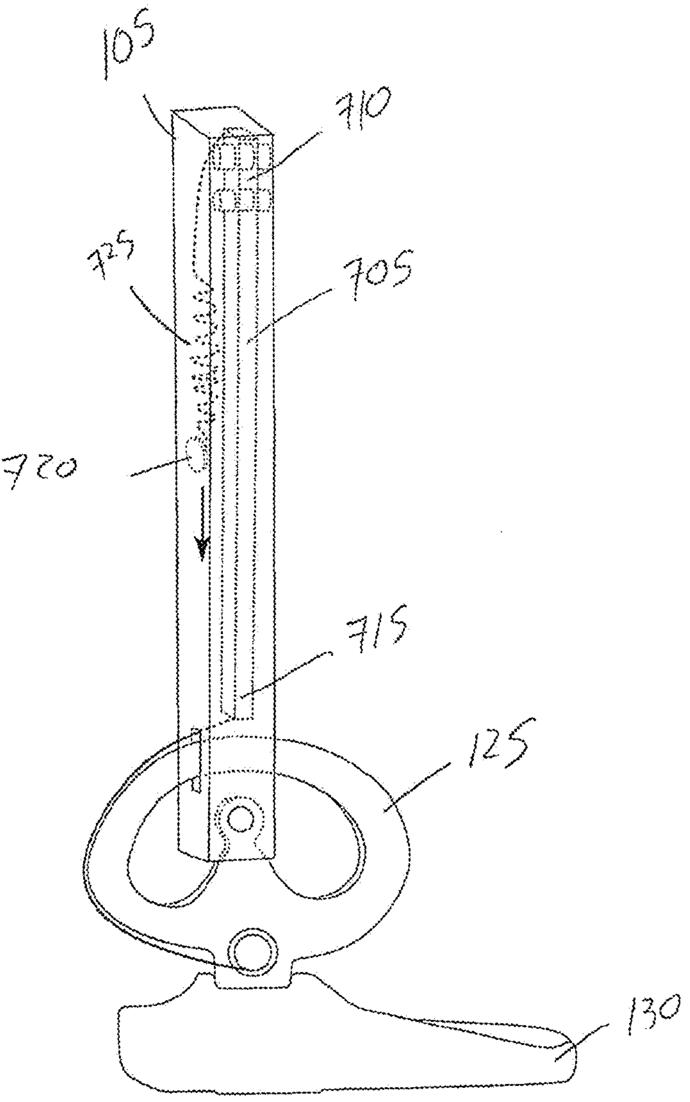
FIG. 7A depicts a passive spring-based mechanism for dynamic leaf spring pivot adjustment.

While the leaf spring embodiments described above in reference to FIGS. 3 and 3A and 4 contemplate externally mounted leaf springs, this is not a requirement. FIG. 7A shows a variable stiffness AFO having a leaf spring that is internal to the tubular upright member 105. The AFO of FIG. 7A, like those discussed above, has a hollow, tubular upright member 105. A stiffening component, in the case of FIG. 7A, a leaf spring 705 is located within the member 105, and is fixedly or adjustably mounted to an interior surface of member at a proximal or first end 710. A distal end 715 of leaf spring 705 is attached to a force transmission mechanism (e.g., a cable, chain, etc.), which is attached to pulley 125. The leaf spring 705, when deflected from its equilibrium position, pulls on the cable, exerting rotational force on the pulley 125 tending to rotate the attached footplate 130 in a downward or plantar extension direction. Thus, the footplate is rotated up, in dorsi extension as during a preparation for heel strike, the cable flexes the leaf spring, which exerts a resistive force on the pulley, which will tend to return the foot plate to a level position. This stiffens the device during the toe-up, heel-down movement. Flipping the orientation of the leaf spring, the direction of the cable, and the attachment point on the pulley reverses the application of the spring force, creating resistance when the footplate is rotated down. A pair of leaf springs, arranged on opposite interior walls (i.e., front and back walls) of the tubular member may be used to provide stiffening during rotation in both directions.

The extent of the stiffening provided by leaf spring 705 may be adjusted by vertical movement of a translatable pivot 720 on which leaf spring 705 rides. Moving the pivot 720 up lengthens the free distal portion of the leaf spring, thereby making it less stiff, while moving the pivot down shortens the leaf spring's free distal portion, thereby making it stiffer. In one embodiment, the vertical position of pivot 720 may be manually adjusted to vary the amount of stiffness imparted to the AFO by the leaf spring. Alternatively, a mechanized means for adjusting the position of the pivot may be provided, such as those discussed above in reference to FIG. 4.

Thus far, embodiments that are manually adjustable and adjustable via a motorized actuator have been described. The embodiment of FIG. 7, however, provides for a fully-passive (i.e., not powered) but dynamic leaf spring pivot point adjustment. The dynamic pivot point adjustment mechanism may incorporate a mass-spring system that changes position based on the motion of the user. For example, in a lower-extremity configuration, the mass-spring system may extend downward upon heel-strike, lowering the pivot point and automatically adjusting the leaf spring stiffness. Larger accelerations caused by more-forceful heel-strikes (e.g., caused by running) would extend the pivot point downward to increase leaf spring stiffness.

In this alternative embodiment, including optional components also illustrated in FIG. 7A, the AFO can be dynamically adjusted in terms of stiffness without the need for a mechanized or active driving mechanism like a motor. Such embodiments are useful for providing variable levels of assistance or resistance to the user, for example, during different stages of the gait cycle, or when the user is engaged in running versus walking. In an alternative embodiment, pivot 720 is attached to a spring 725, which exerts upward force on pivot 720, tending to translate pivot 720 in an upward direction until the spring force is balanced by the weight of the pivot. During a heel strike, the AFO (including the spring mounting point) experiences a sudden deceleration of its velocity in the downward direction. The AFO stops suddenly, but the pivot continues to move down, momentarily overcoming the spring force. In its new position, the pivot effectively shortens the free end of the leaf spring, increasing its strength and the resulting resistance it provides to certain ankle movements (in the case of FIG. 7A, the resistance to plantar extension movements is increased).

Figure 7B:
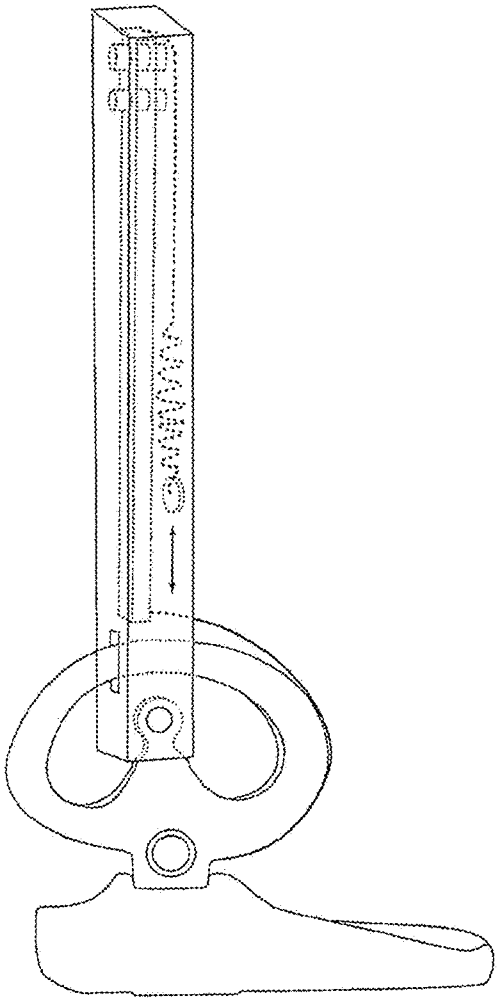
FIG. 7B depicts a passive spring-based mechanism for dynamic leaf spring pivot adjustment having a different orientation.

FIG. 7A illustrates a single leaf spring creating resistance to dorsi extension, and having a pivot point that can be dynamically adjusted upward and downward through the use of the device. It is contemplated that the mechanism shown in FIG. 7A can flipped, so that it provides resistance to plantar extension. Such an embodiment is illustrated in FIG. 7B. In this embodiment, the leaf spring is mounted to a back (posterior) wall of the tubular member, where in the FIG. 7A embodiment, a single spring is mounted to the front (anterior) wall of the tubular member. In the FIG. 7B embodiment, at heel strike, the pivot moves down by the sudden deceleration of the AFO. As the user moves through mid-stance to toe-off, the heel comes up, and footplate rotates down. This pulls against the leaf spring which is now shortened against the pivot, so it is stiffer. During swing, the foot rotates back to level, assisted by the stored energy in the spring, and then to toe-up in preparation for the next heel strike. As this happens, the leaf spring is relaxing, and pivot will tend to translate up, softening the assistance.

It should be appreciated that both mechanisms depicted in FIGS. 7A and 7B may be combined in the same AFO, similar to the arrangement depicted in FIG. 3A, but with the leaf springs internal to the tubular member.

Figure 8:
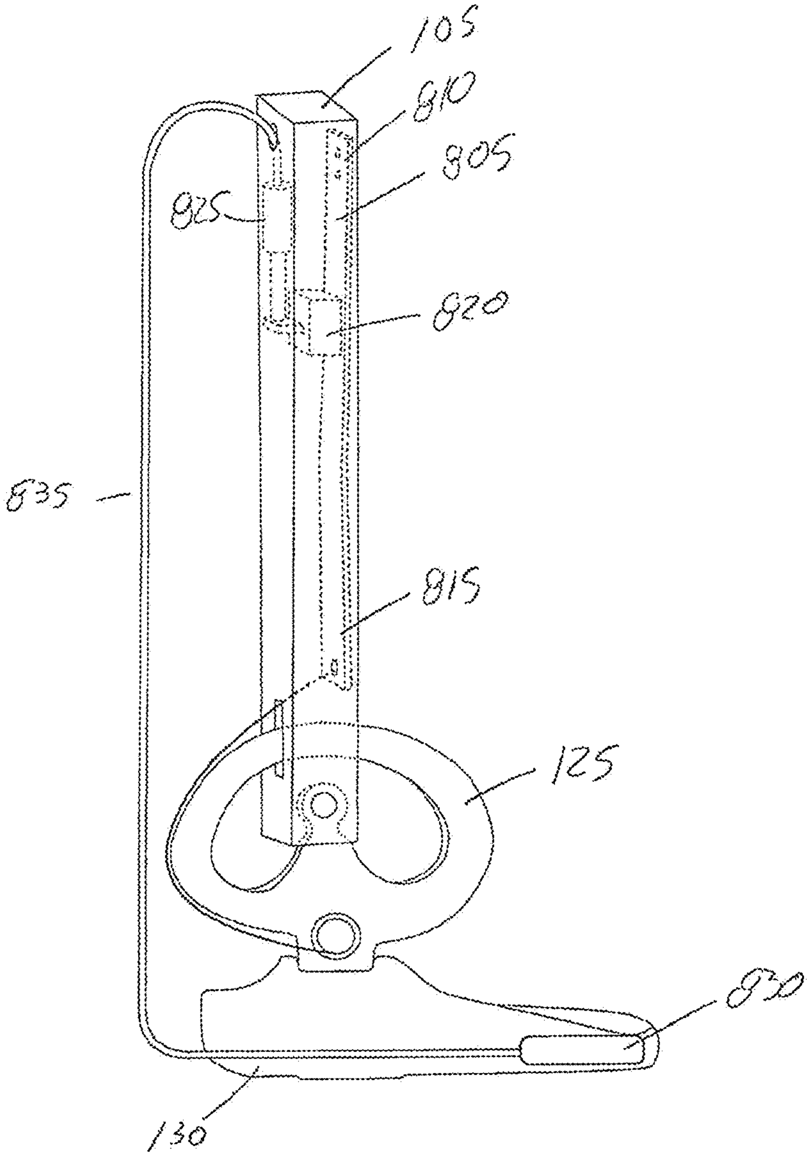
FIG. 8 depicts a hydraulic-piston-based mechanism for dynamic leaf spring pivot adjustment.

Another passive yet dynamic mechanism for adjusting leaf spring pivot point position includes a hydraulic system to transfer pressure from under the foot to a linear slider (or similar) that actuates the pivot point. FIG. 8 illustrates such an alternative dynamic AFO with variable resistance/assistance. In the embodiment of FIG. 8, like that of FIG. 7, a stiffening component, in the case of FIG. 8, a leaf spring 805 is located within the member 105, and is fixedly or adjustably mounted to an interior surface of member at a proximal or first end 810. A distal end 815 of leaf spring 805 is attached to a tensile force transmission mechanism (e.g., a cable, chain, etc.), which is attached to pulley 125. The leaf spring 805, when deflected from its equilibrium position, pulls on the cable, exerting rotational force on the pulley 125 tending to rotate the attached footplate 130 in a downward or plantar extension direction. Thus, in one configuration, when the footplate is rotated up, in dorsi extension as during a preparation for heel strike, the cable flexes the leaf spring, which exerts a resistive force on the pulley, which will tend to return the foot plate to a level position. This stiffens the device during the toe-up, heel-down movement. Flipping the orientation of the leaf spring, the direction of the cable, and the attachment point on the pulley reverses the application of the spring force, creating resistance when the footplate is rotated down. A pair of leaf springs, arranged on opposite interior walls (i.e., front and back walls) of the tubular member may be used to provide stiffening during rotation in both directions.

The embodiment of FIG. 8 includes a vertically moveable pivot 820, which translates vertically within member 105. As with the pivot in the FIG. 7 embodiments, locating the pivot closer to the distal end of leaf spring 805 makes it stiffer, and locating the pivot closer to the proximal end makes it stiffer. Pivot 820 may be translated down by an attached piston, which is part of hydraulic assembly 825. Hydraulic assembly 825 is connected via hydraulic fluid line 835 to a compressible hydraulic bladder 830. When bladder 830 is compressed, hydraulic pressure is transmitted to the hydraulic assembly, which actuates the piston, causing the pivot to translate in a downward vertical direction. The pivot can be retracted in the vertical direction by the relaxation of hydraulic pressure, which will occur when bladder 830 is no longer compressed. A non-illustrated spring may be included to assist in the vertical translation of pivot 820.

In operation, when a user applies downward pressure to the footplate 130, the bladder is compressed causing the pivot to move downward, shortening the free end of leaf spring 805. This will tend to stiffen the spring and increase resistance during toe-down movements, like the transition to terminal stance, right before toe-off. As the foot comes up, the hydraulic pressure drops, and the pivot translates up, weakening the spring, which then provides less resistance to two-up movement, as before heel strike.

As with FIG. 7, it is contemplated that the leaf spring orientation and the position of the pivot can be flipped, and that two assemblies can be provided, on each of the front and back walls of the member 105 to provide assistance/resistance in both angular directions.

Throughout this disclosure AFO's have been described in the context of unilateral devices for one ankle, however, this is not a requirement. It is contemplated that pairs of devices such those described herein will be used, one for each ankle of a user, and such devices are squarely within the scope of the invention.

Thus far, the present disclosure has been directed to assistive devices, described in reference to exemplary AFOs, which use spring elements to store energy created by a user's ankle/foot movements during certain stages of the gait. The spring elements then return this stored energy to the user in the form of assistive torque during certain stages of the gait. The springs can be positioned to undergo tensioning at various different stages of the angular rotation of the pulley/footplate. The springs can also be positioned such that they work against each other, to various degrees, at various different stages of the angular rotation of the pulley/footplate. This permits the applied torque curves to be tuned to create, for example, softening or stiffening resistance (or weakening or strengthening of assistance) at different stages of the angular rotation of the pulley/footplate. The concepts described thus far described allow for the design of passive (i.e., non-motorized) devices, and for devices where the role of actuators is limited to changing the strength of the springs.

In other embodiments, the concepts here before described are applied to active exoskeletal AFOs. Active AFOs generally use one or more actuators, such as motors, to apply assistive torque to a joint of the user during various stages of a gait cycle. These devices may also provide resistive torque. Generally, an active AFO will have a pair of wearable, battery powered, counter-rotating motors, one for each limb, each motor connected to a pair of force transmitting linkages (preferably Bowden cables). Each pair of Bowden cables is connected to a pulley, which is connected to a footplate. When a motor rotates in one direction, the footplate rotates in a toe-up direction, and when the motor rotates in the opposite direction, the footplate rotates in a toe down direction. This applied assistive torque assists a user with walking. Again, these devices may be configured to provide resistance rather than assistance. An exemplary powered AFO is described in U.S. Patent Publication No. 2019/0343710, entitled "Exoskeleton Device," the entirety of which is incorporated herein by reference.

The passive spring-based energy storage concepts outlined above may be combined with a powered exoskeletal AFO, in a parallel configuration, to combine active (i.e., actuated) and passive (i.e., spring-assisted) components to improve the performance of either component independently. Such devices may use springs having adjustable stiffness, to allow the devices to be tuned to each user's preferences, needs or body mass. When configured I parallel to the powered actuation system, the spring components can offload motor requirements to result in a lighter weight exoskeleton design, save battery capacity, and/or increase battery life. Additionally, the spring can increase the amount of torque and positive powered force provided to the user at very low cost and low added mass.

In one embodiment, a powered ankle exoskeleton is provided, which provides plantar-flexor and/or dorsi-flexor assistance during walking or running. During certain phases of the gait cycle, like stance phase, a parallel leaf spring coupled to the pulley engages (stores and returns elastic energy as the lower-limb naturally dorsi-flexes), which offloads assistive torque and/or power output requirements from the motor. This leaf spring design allows for change in stiffness by changing the leaf spring and also a rapidly adjustable pivot point, which changes the spring stiffness without replacement so that it can be customized to each user, their body mass, or ambulatory condition (e.g., slow walking, fast walking, running). In another embodiment, the exoskeleton is used to provide resistance during walking or running, and the leaf spring is engaged in an opposite direction (off-loading the required resistive torque and/or power output from the motor).

Figure 9:
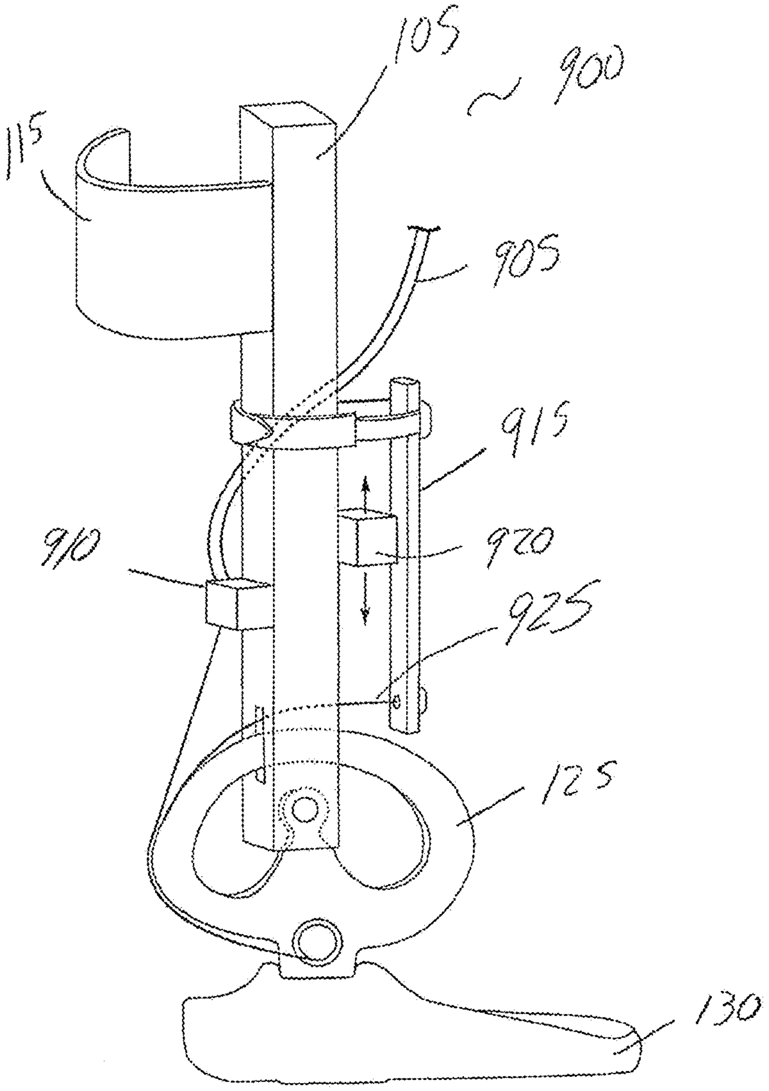
FIG. 9 depicts a powered AFO with a parallel mounted spring for additional assistance.

One such example incorporating the concepts outlined above is depicted in FIG. 9. There is shown the lower portion of an AFO 900. The AFO has an upright (vertical), tubular member 105 such as those described above. A rotational bearing carries a rotational element such as a pulley 125 within the interior walls of member 105. The pulley 125 is coupled to a footplate 130. A tensile force transmission mechanism (cable, cord, ribbon, chain, etc.), but preferably a Bowden cable 905, has a distal end that is coupled to one side of pulley 125. In the case that mechanism 905 is Bowden cable, the sheath may be anchored at an anchor point 910 on or near member 105, and near pulley 125. The cable 905 has a proximal end that is coupled to a non-illustrated actuator such as a wearable, battery powered motor operable to pull on the cable, and then allow the cable to extend again when subject to pulling force. In the example of FIG. 9, the motor and cable are operable to provide ankle torque in a plantar-extension, or toe-down direction to provide assistance while working, or to provide dorsi extension resistance. The embodiment of FIG. 9 also includes spring 915, which in this example is a leaf spring. Spring 915 is mounted to a wall of member 105 at a top or proximal end. Spring 915 is coupled to a tensile force transmitting mechanism 925 (e.g., a cable), at a bottom or distal end. The cable couples the spring to the pulley. In the configuration as shown, when the user rotates footplate in a toe-up direction (e.g., in preparation for heel strike), spring 915 is tensioned. The stored energy is then released as the spring applies toe-down torque to the pulley/footplate as the user proceeds through mid-stance to toe-off. This provides assistance to that movement, and it reduces the amount of powered torque assistance needed from the motor for the movement.

The device of FIG. 9 also includes a pivot 920, which may be adjusted in terms of its position so that it may contact the leaf spring 915 at variable positions along its length. The pivot may be slid and secured by the user manually, or it may be moved by an actuator as set forth in the embodiments above. The positioning of the pivot may be the user's decision, or it may be determined automatically, for example, in accordance with the methods discussed in reference to FIGS. 4-5. The positioning of the pivot varies the length of the free end of the spring 915, which adjusts the spring's strength.

While the example of FIG. 9 shows a spring providing parallel assistance for a single actuated cable for plantar-extension, other configurations are possible and within the scope of the invention. A device with a pair of actuated cables connected to one or more counter-rotating motors providing both dorsi and plantar extension is contemplated. The use of one or two leaf springs, each for a different rotational direction is also contemplated. Leaf springs that work against the actuated direction, to reduce assistance or otherwise tune the response curve are possible. Any combination or positioning of leaf springs, in combination with any combination or positioning of actuated cables is within the scope of this disclosure.

Figure 10:
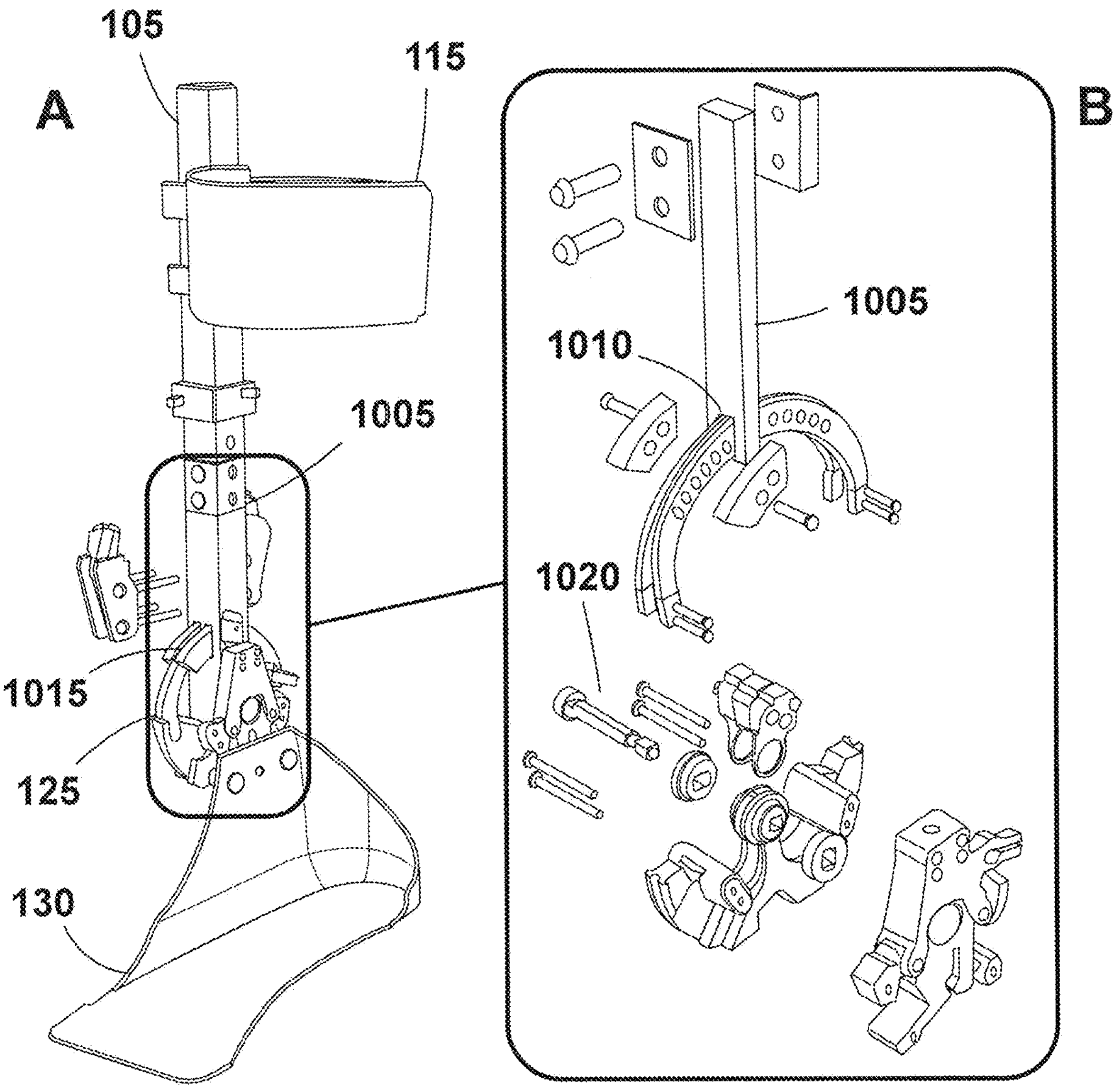
FIG. 10 depicts an alternative embodiment of a powered or passive AFO having an internally mounted leaf spring.

An alternative embodiment of a passive assistive AFO is shown in FIG. 10. The device of FIG. 10 includes a hollow, upright member, again, preferably made of carbon fiber, and a medially projecting user attachment device 115, such as a calf cuff. Inside the member is mounted a vertically arranged leaf spring 1005 (e.g., an elastic carbon fiber bar), which is mounted at a proximal end to an inside wall of member 105. Mounting can be done with a stand-off block ("1"), a cover ("3") and fasteners as illustrated in the magnified portion of the figure denoted as "B". The device includes a footplate 130, coupled to a pulley 125, which rotates with a rotational bearing mounted through side walls of the member 105, such that the side surfaces of the pulley are within the member side walls. An upper portion of the pulley 125 is removable (the removable section denoted as "4"), and this portion passes in a slot or aperture in the member 105. The upper portion of the pulley 125 also passes through a slot or aperture in the leaf spring 1005 at position 1010. This slot or aperture has a width that clears the width of the upper portion of the pulley, but does span the entire width of the anterior and posterior surfaces of the spring 1005. This will allow for an interference to occur between stops 1015 (also denoted "5" in B) and the leaf spring, as will be discussed below. The pulley 125 includes a rotational bearing that rotates around axle pin 1020, which is secured by and between medial and lateral walls of the member.

In certain embodiments, the components illustrated in FIG. 10 are part of a powered device, where a pair cables, e.g., Bowden cables, are coupled to the pulley to provide powered dorsi and plantar extension assistance. In such cases, these cables will be coupled to a non-illustrated battery powered motor that can provide tension and therefore rotation and counter rotation to the pulley. In these embodiments, the device may include a pair of Bowden cable tensioners (as marked in A) to which the sheaths of the Bowden cables are mounted. The tensioners may include barrels that allow the tension between the sheaths to be varied with respect to the inner cables. In active devices the footplate 130 may be attached to the pulley 125 via an optional strain sensor and mounting block ("8" in B), which may be useful for data collection and computing desired supplied power ankle torque. In alternative passive embodiments, the footplate may mount directly to the pulley without an intervening sensor block. Active or passive devices may also include other sensors, such as an angle encoder ("6" in B) or other angle position, velocity, or acceleration sensor, and one or more pressure sensors on the footbed.

In the device of FIG. 10, one or more stop assemblies 1015 may be affixed to the pulley 125 at a variety of positions along the pulley's perimeter. In one case, there are a number of fixed positions the stop assemblies can occupy, but alternatively, the stop assemblies could be slid along continuously and fixed at a continuum of positions, using a tensioning mechanism. Fixed positions may be preferable because the stop assemblies must resist a large amount of shearing force in operation. The positions of the stop assemblies along the pulley determine the angular position of the pulley at which the leaf spring 1005 is engaged and deflects. Referring now to stop assembly 1015 in A, as the footplate pictured is rotated into a more toe-up position, the leaf spring will be engaged and will store energy, which will be returned as the foot is rotated back down. Another stop assembly on the anterior side of the leaf spring will perform the same function for toe-down rotation. By adjusting the positions of the stops, the angles at which resistance begins can be changed.

In alternative embodiments, the device of FIG. 10 may include one or more adjustable or fixed pivots arranged within the member 105. These pivots are arranged between the leaf spring and the interior surfaces of the member such that the spring engages the pivot when it deflects in the direction of the pivot. The pivots can be slid up or down the length of the leaf spring, by the user, to change the strength of the spring for a given direction of rotation. A pivot on the anterior side of the spring will stiffen the spring against footplate rotation in a toe-up direction as the pivot moves down. A pivot on the posterior side of the spring will stiffen the spring against footplate rotation in a toe-down direction as the pivot moves down. Both pivots are independently adjustable and fixable by the user.

Figure 11:
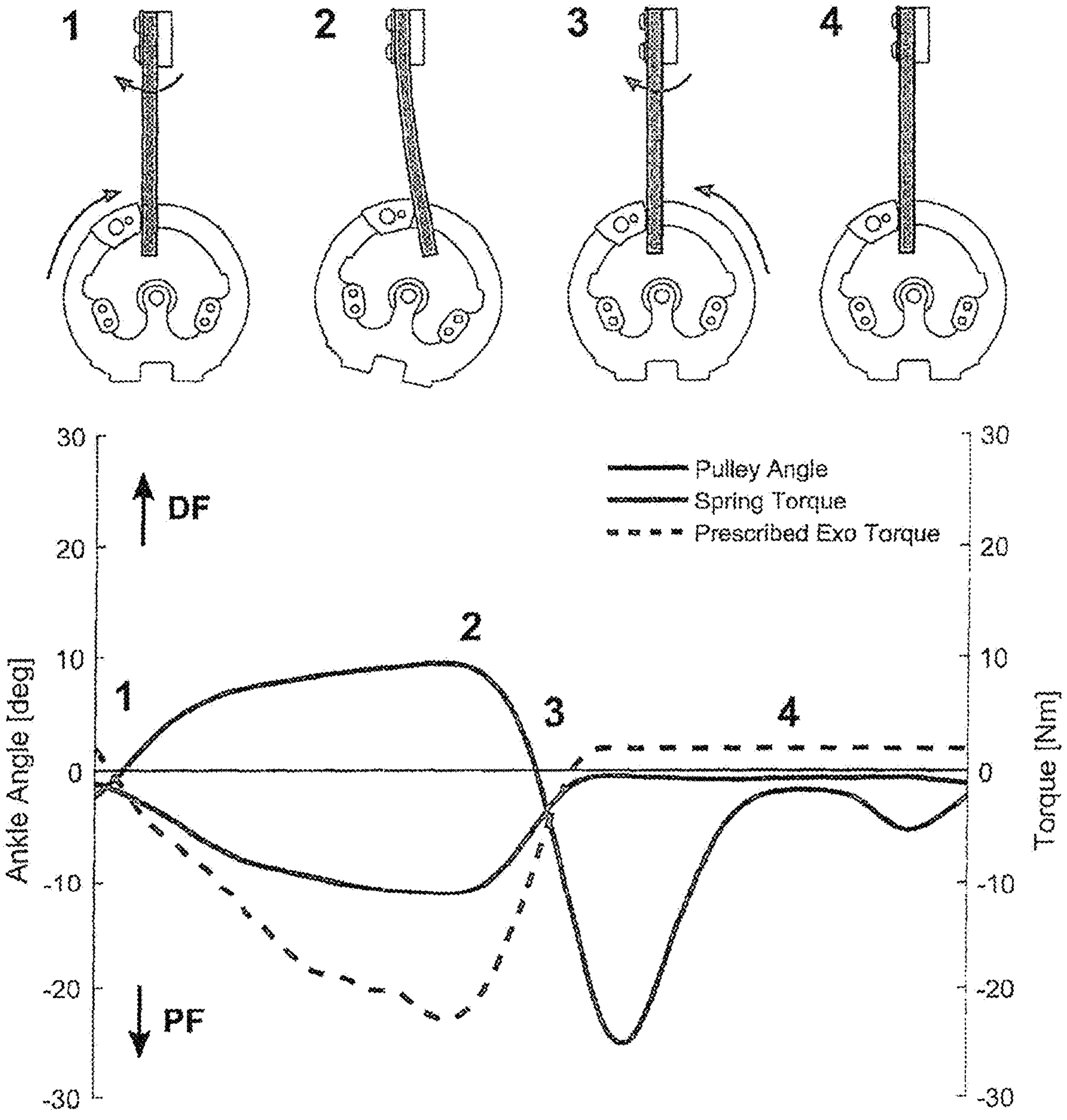
FIG. 11 depicts the operation and torque profile of the embodiment of FIG. 10.

FIG. 11 shows how the device of FIG. 10, in one configuration with a stop assembly placed as shown, will store and return torque to the pulley/footplate thought the stages of the gait. Here, the stop is placed on the anterior side of the pulley and engages the spring upon rotation in the dorsi flexion (toe-up) direction. As can be seen, the spring provides increasing resistance and energy storage during the stance. During the mid to late stance push-off phase, the spring returns the energy as the foot rotates to level, and the spring is not, or is minimally, engaged as the user rotates the foot forward during the swing phase. In the case of an active assistive device, the prescribed assistive torque during these movements may be represented by the dotted line ("prescribed external torque"). As can be seen, the torque curve of the passive spring matches the prescribed torque curve quite well, suggesting that the spring can be helpful in reducing the amount of torque delivered by the motor of the active device, at all gait stages. An engagement clutch may be used to engage the previously described dorsi flexion resistance spring at heel strike and release the dorsi flexion resistance spring at toe-off to allow for unresisted dorsi flexion during the swing phase. As depicted, the motor may need to overpower the dorsi flexion resistance spring during swing phase; however there would be a net positive/beneficial effect for the spring offloading the motor across the entire stance phase because the ankle is in greater dorsi flexion during stance phase than during swing phase.

Figure 12:
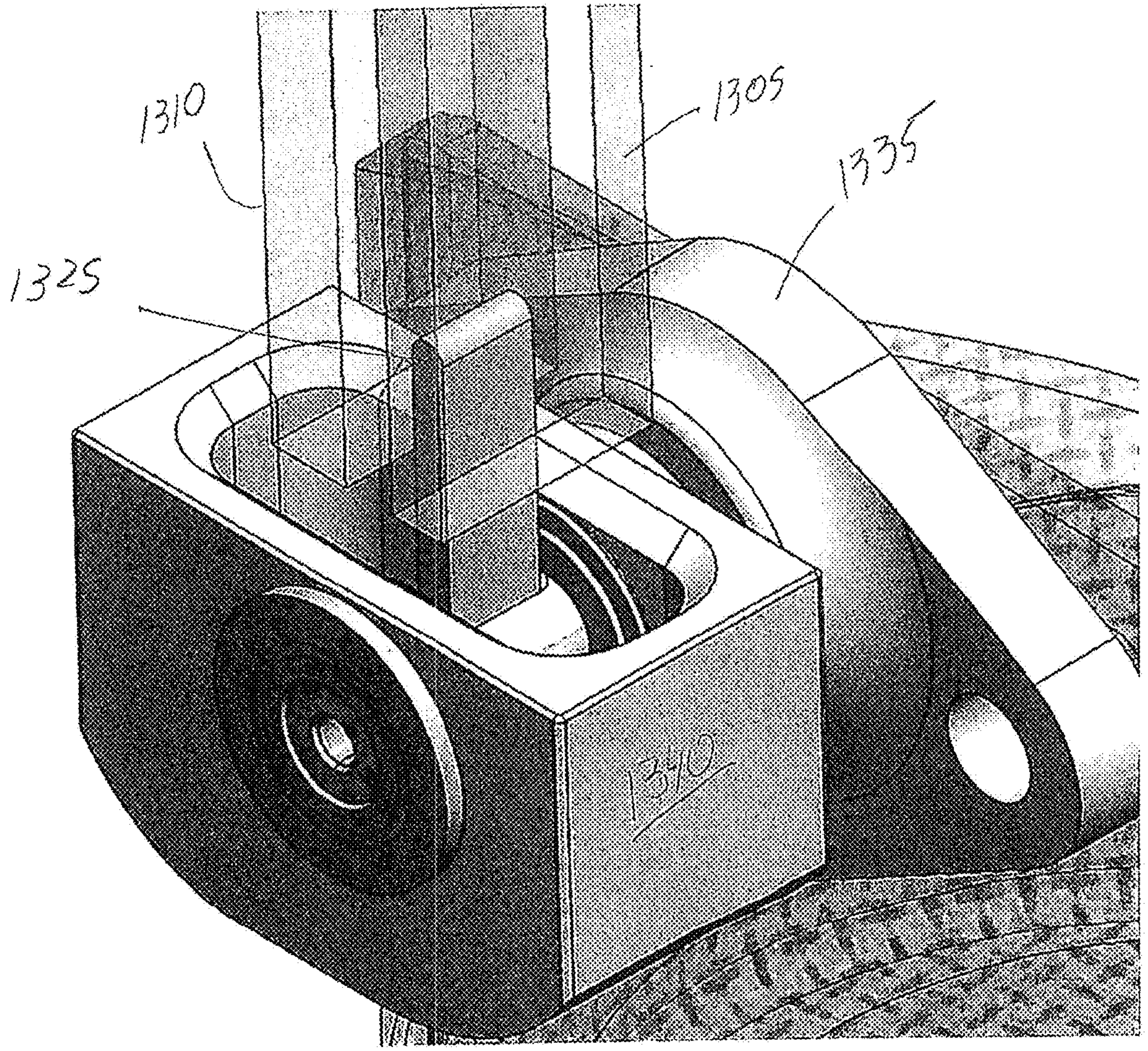
FIG. 12 depicts an AFO having a pair of internally mounted leaf springs.
Figure 13:
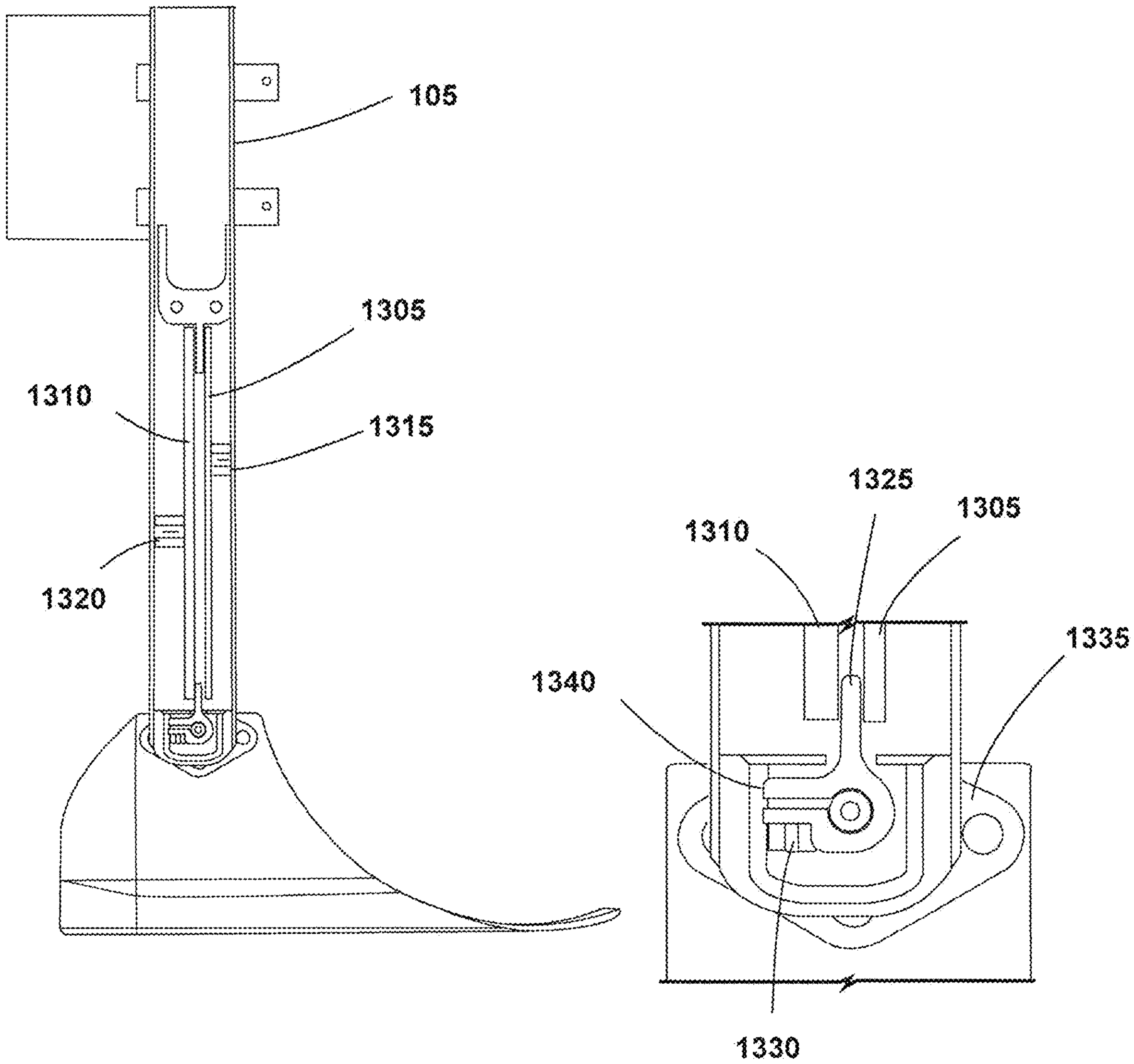
FIG. 13 depicts an alternative view of the passive AFO of FIG. 12.

FIGS. 12 and 13 illustrate an alternative assistive device incorporating a pair of vertically mounted, spaced apart leaf springs, preferably arranged within the hollow upright member of the device. In the arrangement of FIGS. 12 and 13 a posterior spring 1310 and an anterior spring 1305 are arranged on posterior and anterior sides of the upright member 105. These springs are mounted to the member 105 at their proximal ends. The device also includes a pair of spring pivots 1315, 1320, which may be slid vertically between the interior walls of the member and the springs, and fixed in position, where they will be engaged by their respective spring. This allows a user to set the strength of each spring, as in the embodiments described above. A rotational hinge element 1340 includes a bearing, which may receive a non-illustrated axle pin, which is secured by and between the medial and lateral walls of the member, as in the embodiment of FIG. 9. Thus, hinge element 1340 is arranged within the member and rotates with respect to the member. The hinge element 1340 is coupled to a mounting block 1335 (e.g., through an aperture in a medial sidewall of the member), which is coupled to a footplate. Again, this permits the footplate to rotate with respect to the member and the rotational hinge element.

The rotational hinge element 1340 includes a tab or projection 1325 which projects upwardly and is arranged between the distal free ends of the leaf springs. When the footplate rotates in a toe-up direction, the tab engages the anterior leaf spring 1310, and when the footplate rotates in a toe-down direction, the tab engages the posterior leaf spring 1305. In each of these movements, the spring stores energy, and returns it as torque to the footplate when it counter-rotates.

In certain embodiments, the tab 1325 is mounted to the bearing portion of the hinge mechanism 1340 via a clamp 1330. The clamp 1330 may be loosened and retightened to allow the user to change the angle between the tab 1325 and the remainder of the hinge mechanism 1340. This allows angular adjustment to be made between the footplate and the tab, which allows the user to set the equilibrium angle of the footplate, i.e., the angle at which the footplate rests before further motion in either direction engages either spring.

Figure 14:
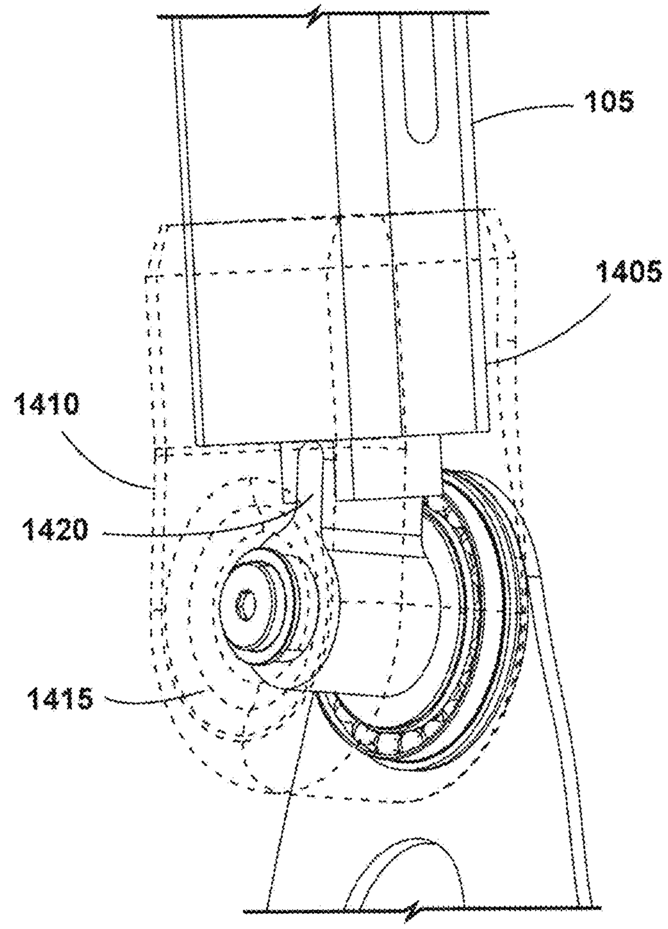
FIG. 14 depicts an equilibrium adjustment mechanism usable with the embodiments described herein.

FIG. 14 shows an alternative arrangement for adjusting the equilibrium angle of the footplate and the spring-engaging tab. In the embodiment of FIG. 14, the distal end of member 105 includes a termination cap 1405, which defines a through aperture. The aperture receives a non-illustrated axle pin. A rotational bearing 1415 is secured within the cap and rotates around the axle pin. The rotational bearing 1415 includes an upwardly extending tap 1420, which extends up between the distal ends of non-illustrated leaf springs. The rotational bearing 1420 has on a medial side teeth, which engage corresponding teeth on an upper tab coupled to the footplate. The footplate tab and the rotational bearing can be held in tension by non-illustrated one or more fasteners such that the two parts rotate with respect to the member together. The fasteners may be loosened, and the relative positions of the rotational bearing and the footplate tab can be changed. This has the effect of changing the angle of the footplate with respect to the tab, which allows for the equilibrium angle of the footplate to be adjusted.

As is set forth above, primarily in connection with FIGS. 5 and 10, in certain embodiments the elements described hereinbefore may be used in a powered device, that provides assistance or resistance to a user actuating the user's joint. In certain embodiments, the device includes sensors, such as an angle encoder at the ankle, and a pressure sensor under the footbed. These sensors may be used to gather data usable to, among other things, compare the user's interaction with the device with preset thresholds to determine the user's progress in a rehabilitation program, increase or decrease the stiffness of passive components like leaf springs, or increase or decrease the amount of resistance or assistance supplied by an active device. In certain embodiments, measurements relating to the user's interaction with the device may be used to generate biofeedback intended to reinforce or modify the user's use of the device, for example, to encourage a user to walk normally, or in accordance with certain predetermine performance metrics.

In co-owned U.S. patent application Ser. No. 17/534,891, entitled "Exoskeleton Device," Applicants described an active or passive orthosis for providing assistance or resistance to a user's joint, such as an ankle. In that disclosure, Applicants described providing an array or sensors in a powered orthosis that measured the user's walking performance with an orthosis, compared the user's performance with predetermined performance metrics, and then provided feedback to the user through a feedback modality to encourage the user to meet performance targets. The entirety of U.S. patent application Ser. No. 17/534,891 is incorporated herein by reference for all purposes, but pertinent disclosure from that reference will be provided here for clarity. It should be understood that the elements below, many of which relate active ankle and/or knee orthoses using motors and Bowden cable driven pullies to provide assistance or resistance, may be combined with any of the embodiments described above.

Figure 15:
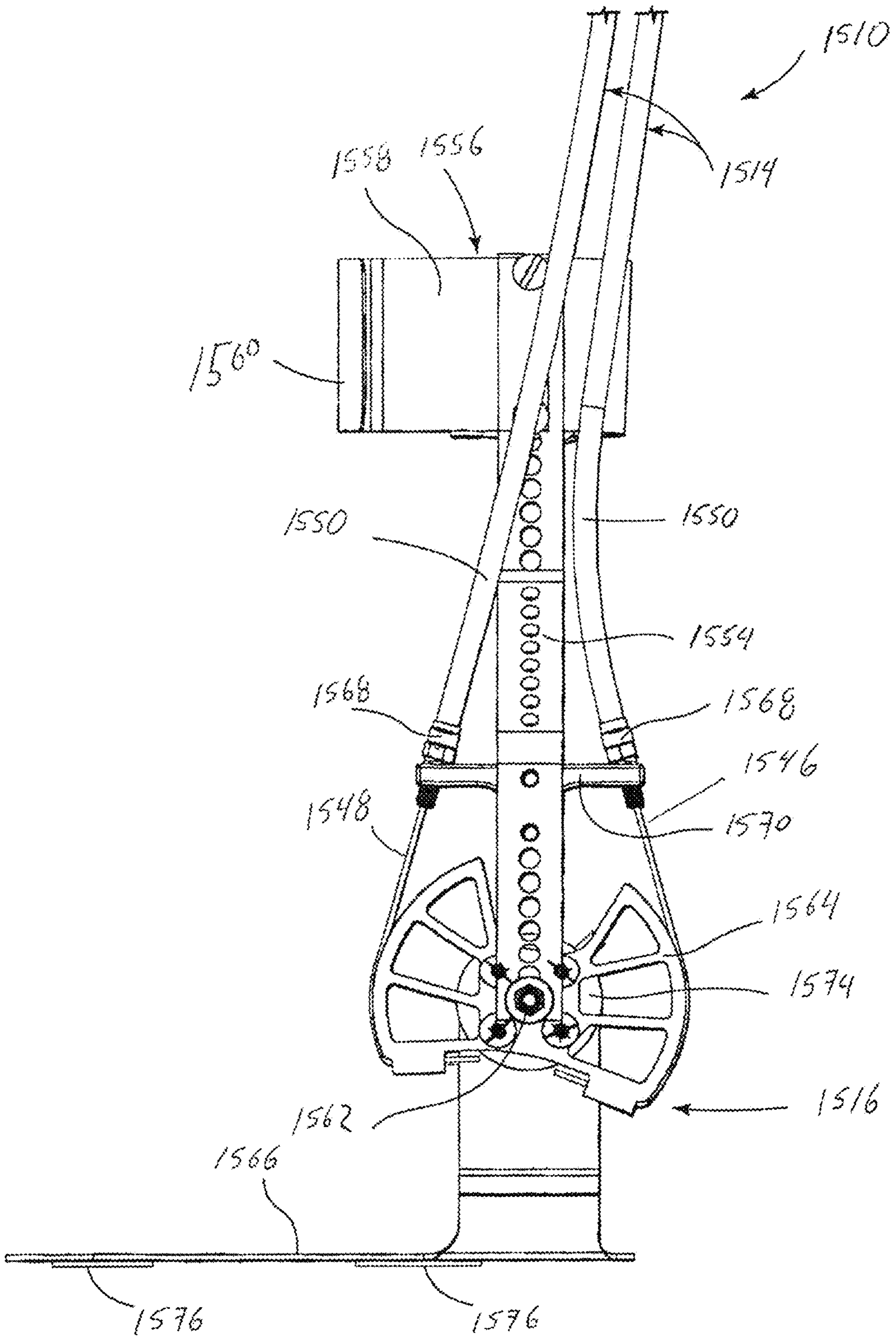
FIG. 15 is a side plan view of a lower hinged assembly that is operably coupled with the control unit through a transmission assembly, according to some embodiments.
Figure 16:
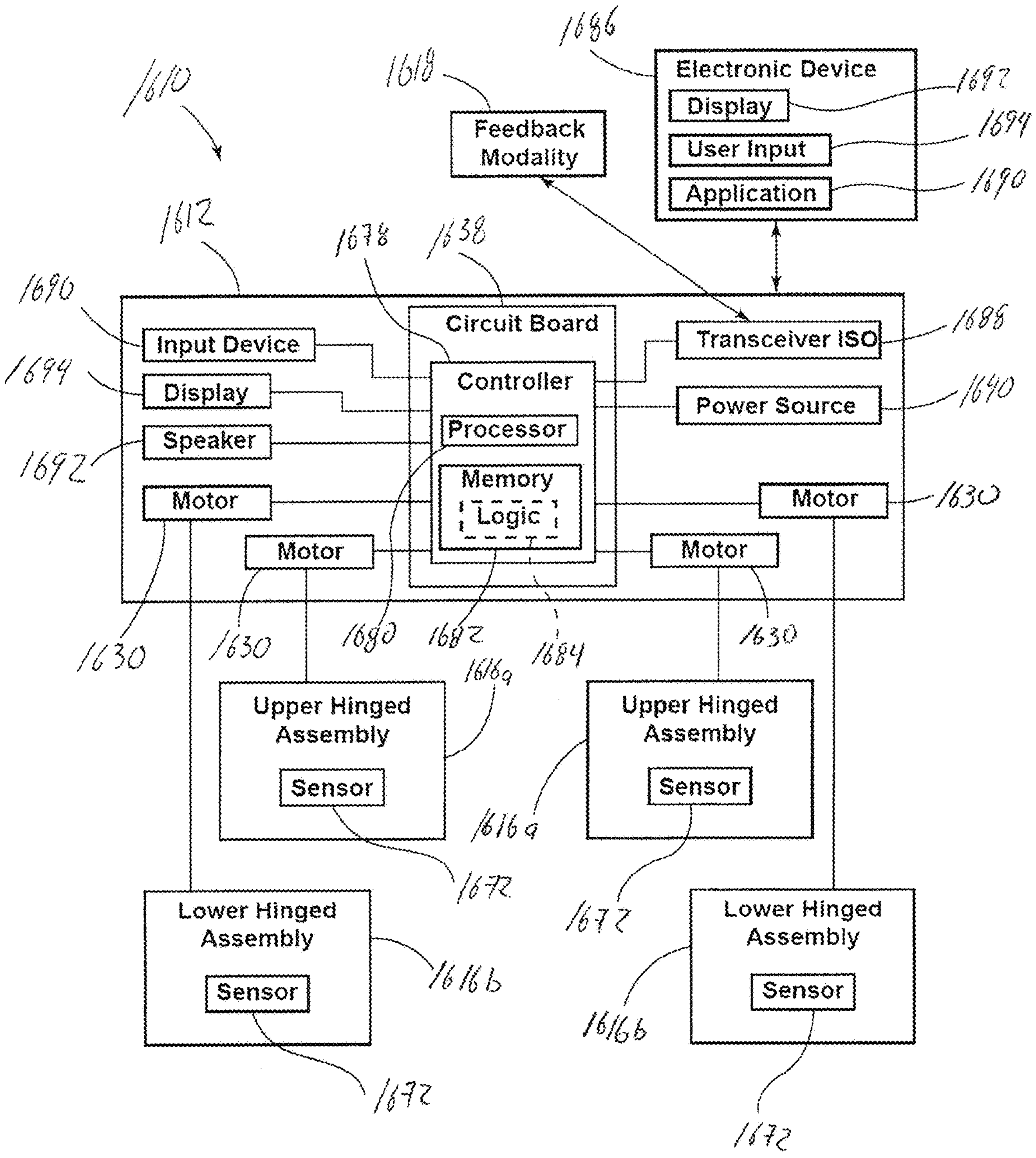
FIG. 16 is a block diagram of the exoskeleton device, according to some embodiments.

FIG. 15 illustrates a lower limb exoskeleton device 1510, to be worn on the lower leg of a user, and to be used for providing assistance or resistance to the user's ankle during walking. Exoskeleton device 1510 is coupled, both electronically, and via force transmission assemblies 1514 (e.g., Bowden cables) to an unillustrated control unit. The control unit takes measurement data from device sensors, provides electronic control of the device, includes one or more actuators to apply rotational force to a footplate 1566 through a pulley 1564 and transmission assemblies 1545, and may also provide user feedback through a feedback modality, as is shown in the example of FIG. 16, below. In some embodiments, an assistive device includes a control unit, a pair of transmission assemblies 1514, a pair of exoskeleton devices 1510, and a pair of hinged assemblies 1516, such that both ankles can be provided with assistance or resistance. In other embodiments, four hinged assemblies are provided: one pair for the knees and one pair for the ankles. One of these embodiments is illustrated schematically in connection with FIG. 16, below.

Referring again to FIG. 15, force generated by the one or more actuators in the control unit can be carried by one or more transmission elements of the transmission assembly. The transmission elements are configured to provide force to various elements of the exoskeleton device that can be remote from the control unit. For example, cams, linear shafts, pistons, universal joints, and other force-transferring linkages may be implemented. In embodiment illustrated in FIG. 15, the transmission assembly 1514 includes one or more extension cables 1546 and one or more contraction cables 1548. The extension cables 1546 and contraction cables 1548 may be arranged to transfer opposing forces due to the suitability of cables for transferring "pulling" forces but not for transferring "pushing" forces. In some embodiments, a single transmission element may be used to transfer opposing (both pushing and pulling) forces.

In the embodiment of FIG. 15, the transmission assembly 1514 is routed down one or more legs of a user to reach the lower hinged assembly 1516. In the illustrated example, the transmission assembly 1514 is lightweight and flexible so as to allow minimal impediment of motion of the knee and hip joints of a user. The exoskeleton may include one or more lubricating fluids or materials, disposed on an element or between two relatively-moving elements to reduce friction and increase efficiency. The extension cables and contraction cables may be formed from any suitable material, with examples including metal, Kevlar, and nylon.

The one or more extension cables and one or more contraction cables may each be housed in a cable sheath. The one or more cable sheaths may serve to support and house the extension cables and contraction cables. In the embodiment illustrated in FIG. 15, the extension cables 1546 and contraction cables 1548 may be Bowden cables that transfer force via the movement of inner cables relative to a hollow sheath 1550 or housing containing the inner cable. The one or more cable sheaths 1550 may each be coupled to barrel adjustors 1568. The barrel adjustors 1568 allow for adjustment of the length of the sheaths 1550 to adjust a baseline tension of the extension cables 1546 or contraction cables 1548. The one or more barrel adjustors 1568 may be further coupled to the one or more cable brackets or support blocks 1570, which are coupled to upright member 1554.

In the embodiment illustrated in FIG. 15, lower hinged assembly 1516 includes an upright member 1554 that serves as a mounting or support element for the components of the lower hinged assembly 1516. Upright member 54 may be additionally coupled to an orthotic cuff 1556. The orthotic cuff 1556 may be additionally coupled to a D-ring strap 1558 and a Velcro strap 1560. The orthotic cuff 1556, D-ring strap 1558, and Velcro strap 1560 may be considered together as an attachment mechanism for coupling the lower hinged assembly 1516 to a leg of a user at an attachment site, which may be between an ankle and a knee of the leg of the user.

Each upright member 1554 may be additionally coupled to a bearing 1562 or joint proximate an opposing end portion from the orthotic cuff 1556. The one or more bearings 1562 may each be coupled to a sprocket or pulley 1564. Each of the one or more bearings 1562 may serve as a freely-rotating and load-bearing connection between the upright member 1554 and the sprocket 1564. Each collection of an upright member 1554, a sprocket 1564, and a bearing 1562 may be operably coupled to one another through connecting hardware, such as bolts and nuts or other suitable connecting hardware. The connecting hardware may be disposed through various adjustment holes defined by the upright member 1554 for adjustability of the lower hinged assembly 1516 based on the user's body type.

In some embodiments, additional brackets are attached to the lower hinged assembly based on the joint that is to be assisted. For example, as illustrated in FIG. 15, one or more insole brackets 1566 may be rotatably coupled with the upright member 1554. The insole brackets 1566 support the foot of the user and received torque that is to be applied to a walking surface of the user. The one or more insole brackets 1566 may be formed from a metallic material, a polymeric material, and/or any other suitable rigid material. The one or more insole brackets 1566 may be configured to be inserted into a user's footwear using thin elements without external straps. Suitable designs for insole brackets (which may also be referred to as footplates) usable with any embodiment disclosed in this application may be found in co-owned U.S. patent application Ser. No. 17/365,768 entitled "Optimized Ankle Exoskeleton Foot Plate Function and Geometry," which is incorporated by reference herein in its entirety.

After passing through the barrel adjusters 1568 and exiting their sheaths 1550, the extension cables 1546 and the contraction cables 1548 may couple to the sprockets 1564. The sprockets 1564 may clamp to each of the extension cables 1546 and the contraction cables 1548 on a first end portion and coupled to a single actuator pulley in the control unit on a second end portion. In various embodiments, an opposing pair may instead embodied in a single element with the capability to transfer both positive and negative forces. In some embodiments, the sprocket 1564 may include any device for capturing force from a transmission assembly 1514 to produce torque between two or more attachment points with at least one attachment point on each side of a user's joint (e.g., torque between the insole bracket 1566 and the orthotic cuff 1556).

Each upright member 1554 and insole bracket 1566, taken in combination, may be considered as a force-applying arm applying torque around an axis. In some instances, the axis is generally aligned with a body joint axis (e.g. an ankle joint axis). When a force is applied along a length of extension cables 1546 or contraction cables 1548, a force is applied to sprocket 1564 and, in turn, insole bracket 1566. Accordingly, the forces applied along the lengths of extension cables 1546 and contraction cables 1548 apply a force causing insole bracket 1566 to rotate about the bearing 1562 with respect to upright member 1554.

In various embodiments, the extension cables 1546 and/or the contraction cables 1548 can be actuated based on acquired data from one or more sensors within the exoskeleton device 1510. As provided herein, one or more performance metrics may be determined based on the acquired data, which may include at least one of a posture position, joint positions/angles, joint moment, joint power, or spatiotemporal parameters of walking, including step/stride length and gait speed. In some examples, the one or more sprockets 1564 may each be additionally coupled to a torque sensor or a joint angle encoder 1574 configured to measure an angle at some point during an individual's gait cycle as the data point. The torque sensor may be used to sense the torque force applied by the exoskeleton device 1510 for assistance. The torque sensor may be additionally coupled to the insole bracket 1566, as in the example of FIG. 10, above. In some embodiments, the one or more sprockets 1564 may be coupled to the corresponding one or more insole brackets 1566 without an intermediate torque sensor. Additionally or alternatively, in various embodiments, the sensor may be configured as one or more accelerometers coupled the lower hinged assembly 1516 to provide information on the user's gait. In the case where sensor 1574 is an angle encoder, it may be used to collect data reflecting the angle between lower hinged assembly 1516 and upright member 1554, or two other positions sufficient to determine the angular motion of the user's ankle as it changes over time. In this way, when sensor 1574 is an angle encoder, the user's ankle angular velocity and acceleration can be measured.

In some embodiments, the device may include one or more pressure/force sensors 1576, which may also be operably coupled with the insole bracket 1566. The one or more pressure/force sensors 1576 may be positioned on an upwardly and/or a downwardly facing surface of the insole bracket or footplate 1566 in various embodiments to provide spatial pressure information across the foot surface. The one or more pressure/force sensors 1576 may include force-sensitive resistors, piezoresistors, piezoelectrics, capacitive pressure sensors, optical pressure sensors, resonant pressure sensors, or other means of sensing pressure, force, or motion. Preferably, at least one force sensor 1576 is positioned on the insole bracket such that it measures the force being exerted by the user against the footplate (or through the footplate against a resisting surface such as the ground) underneath the forefoot or ball of the user's foot. A sensor in this location may be used to measure ankle moment, i.e., the force applied times the horizontal distance from the axis containing the axis of rotation of the ankle, which will generally be the distance along the insole bracket to a vertical axis (parallel to member 1554) intersecting the center of bearing 1562.

In some embodiments, the exoskeleton device 1510 may also include a feedback modality (illustrated schematically below in connection with FIG. 16) for providing feedback regarding the individual's use of a wearable exoskeleton device 1510 in a free-living environment. In some instances, a method for providing feedback to an individual using a prosthesis utilizes a computer monitor mounted at line-of-sight in front of a treadmill that provides a near real-time visual display of desired biomechanical parameters and the individual's compliance or non-compliance with these parameters. However, as can readily be determined, this type of feedback can be incompatible with use outside of a rehabilitation facility and in free-living settings. Accordingly, in some embodiments, the exoskeleton device 1510 may utilize other methods for providing feedback that include auditory feedback via speakers or headphones or earbuds, vibrotactile feedback via small vibration actuators, and/or wearable visual feedback via body-warn displays (e.g. wrist mounted monitor or LEDs). The location of these various feedback modalities is not limited, so long as they are positioned and configured to provide perceptible feedback to a user of the exoskeleton device. As one example, vibrotactile feedback may be provided by a vibrotactile actuator positioned to provide vibrotactile feedback to the calf of a user wearing the device.

As is set forth above, embodiments described herein will generally be driven by a control unit including various electrical components for receiving and processing sensor data, providing user feedback and for actuating one or more of the actuators. In turn, the actuators provide force that is transmitted to one or more upper or lower hinged assemblies through the transmission assembly, such as is shown in the example of FIG. 15. These components (hinged assemblies and the control unit) are shown as a schematic exoskeleton device 1610 in FIG. 16. In this example, the control unit 1612 includes a controller 1678 having a processor 1680 and memory 1682 that is powered by the power supply 1640. Logic 1684 is stored within the memory 1682 and includes one or more routines that is executed by the processor 1680, such as the method 106 described in reference to FIG. 19. The controller 1678 includes any combination of software and/or processing circuitry suitable for controlling various components of the exoskeleton device 1610 described herein including without limitation processors, microcontrollers, application-specific integrated circuits, programmable gate arrays, and any other digital and/or analog components, as well as combinations of the foregoing, along with inputs and outputs for transceiving control signals, drive signals, power signals, sensor signals, and so forth. All such computing devices and environments are intended to fall within the meaning of the term "controller" or "processor" as used herein unless a different meaning is explicitly provided or otherwise clear from the context.

In alternative embodiments, the control and/or feedback devices described herein as being associated with the control unit are located in external devices (e.g., desktop computers, laptop computers or handheld devices such as tablets or mobile phones). In these cases the remote controllers communicate with actuators, sensors and feedback modalities through transceivers, which are preferably wireless. Thus, while the control unit is described above as including a processor, this is not a requirement. In certain embodiments, the control unit may not include a processor, but instead may be an actuate unit that contains actuators and transmission assemblies, which actuators are in communication with one or more processors elsewhere.

In some examples, more than one joint on a common limb may be assisted by the exoskeleton device and activated/deactivated by the controller. For example, in some instances, the exoskeleton device may provide assistance to any one or more of an ankle, a knee, and/or a hip of a user. In the embodiment of FIG. 16, the exoskeleton device 1610 includes the control unit 1612, a pair of upper hinged assemblies 1616*a* and a pair of lower hinged assemblies 1616*b*. The pair of upper hinged assemblies 1616*a* may be positioned proximately to respective knees of a user while the lower hinged assemblies 1616*b* may be positioned proximately to the user's respective ankles (as in FIG. 15). In some examples, the exoskeleton device 1610 may include any number of upper hinged assemblies 1616*a* and/or lower hinged assemblies 1616*b* depending on the assistance to be provided to the user.

In the embodiment illustrated in FIG. 16, the control unit 1612 includes four actuators 1630 that respectively control one of the upper and/or lower hinged assemblies 1616*a*, 1616*b*. In some embodiments, a first actuator 1630 can provide a first level of assistance and the second actuator 1630 can provide a second level of assistance. The first level of assistance can be greater than, equal to, or less than the second level of assistance during different phases in which the exoskeleton device 1610 is used. Fewer actuators can be used in cases where the device 1610 includes fewer hinged assemblies (e.g., a single lower assembly for a single ankle).

In some instances, a transmission may include various gear ratios that allow for more than one upper or lower hinged assembly 1616*a*, 1616*b* to be controlled by a common actuator 1630. The actuators 1630 may be disposed in an offset relationship from one another such that the transmission assemblies (e.g., 1514) extending from each of the actuators 1630 towards the upper or lower hinged assemblies 1616*a*, 1616*b* and free of contact from one another within the control unit 1612. It will be appreciated that the upper and lower hinged assemblies 1616*a*, 1616*b* illustrated in FIG. 16 may include any of the components described herein.

The control unit 1612 may further include a display 1694 for providing the status of the operation of the exoskeleton device 1610 and/or operational data. The control unit 1612 may further include an input device 1690 for accommodating various user inputs and/or a speaker 1692, which may also be operably coupled with the control unit 1612, for notifying a user of any desired condition. These input/output devices may be provided separately from feedback modality 1618, or may act as the feedback modality 1618.

As provided herein, any of the upper and lower hinged assemblies 1616*a*, 1616*b* can include any type of sensor 1672, which may communicate with the control unit 1612 in a wired and/or wireless manner. For example, like the lower hinged assemblies 1616*b*, the upper hinged assemblies 1616*a* may also include a torque sensor 1674. The torque sensor 1674 may be used to sense the torque force applied by the exoskeleton device 1610 for assistance. Additionally or alternatively, in various embodiments, one or more accelerometers may be coupled to the upper and/or lower hinged assemblies 1616*a*, 1616*b* to provide information on the user's gait. Additionally, angle sensors along the exoskeleton device 1610 can measure various angles during a gait cycle and may include potentiometers, encoders (e.g., optical encoders), and the exoskeleton device 1610 employing a light source and a light detector capable of calculating an angle of the exoskeleton device 1610. Sensors such as inertial measurement units (IMUs) may also be used to determine acceleration, velocity, position, and orientations on one or more segments of the exoskeleton device 1610 or biological limbs.

In some examples, the exoskeleton device 1610 may communicate via wired and/or wireless communication with the feedback modality 1618 and/or one or more handheld or electronic devices 1686 through a transceiver 1688. The communication may occur through one or more of any desired combination of wired (e.g., cable and fiber) and/or wireless communication mechanisms and any desired network topology (or topologies when multiple communication mechanisms are utilized). Exemplary wireless communication networks include a wireless transceiver 88 (e.g., a BLUETOOTH module, a ZIGBEE transceiver, a Wi-Fi transceiver, an IrDA transceiver, an RFID transceiver, etc.), local area networks (LAN), and/or wide area networks (WAN), including the Internet, cellular, satellite, microwave, and radio frequency, providing data point communication services.

The electronic device 1686 may be any one of a variety of computing devices and may include a processor and memory. The memory may store logic having one or more routines that is executable by the processor. For example, the electronic device 1686 may be a cell phone, computer, mobile communication device, key fob, wearable device (e.g., fitness band, watch, glasses, jewelry, wallet), apparel (e.g., a tee shirt, gloves, shoes or other accessories), personal digital assistant, headphones and/or other devices that include capabilities for wireless communications and/or any wired communications protocols. The electronic device 1686 may have an application 1691 thereon and a display 1695 may provide a graphical user interface (GUI) and/or various types of information to a user. The operation of the various components of the exoskeleton device 1610 may be altered through the usage of the application 1691 and/or information regarding the operation of the components may be provided on the display 1695. The electronic device 1686 may likewise have any combination of software and/or processing circuitry suitable for controlling the exoskeleton device 1610 described herein including without limitation processors, microcontrollers, application-specific integrated circuits, programmable gate arrays, and any other digital and/or analog components, as well as combinations of the foregoing, along with inputs and outputs for transceiving control signals, drive signals, power signals, sensor signals, and so forth.

In some embodiments, the electronic device 1686 may be configured to receive user inputs via the input circuitry 1693. For example, the inputs may relate to an amount of assistance to be provided by the exoskeleton device 1610 or any other information and/or commands. In response, the controller 1678 may activate/deactivate the one or more actuators 1630 to produce force equating to the desired amount of assistance. Accordingly, usage of the exoskeleton device 1610 may be varied through the usage of the application 1691 in addition to or in lieu of usage of the input device 1690. Additionally or alternatively, the electronic device 1686 may also provide feedback information, such as visual, audible, and tactile alerts. In such cases, electronic device 1686 may act as feedback modality 1618 and may provide any sort of feedback described herein as being provided by feedback modality 1618. The feedback information may be provided for any reason, including but not limited to, additional assistance being needed, less assistance being needed, a set number of cycles being reached, a predefined goal being accomplished or not accomplished, etc. The feedback information may be at least partially determined by the sensors 1672, which may include by torque sensors 1674, ankle angle sensors, pressure/force sensors 1676, any calculated parameter derived from these sensors or their measurements, and/or any other sensor within the exoskeleton device 1610.

In some embodiments, the controller 1678 operates a finite state machine to control the operation of the actuators 1630 to provide assistance to a user. For example, the state machine implemented by the controller 1678 may define a number of different states, including early stance, late stance, and swing phases of the user's gait or step cycle that, in turn, control which of the actuators 1630 is operated to apply force to either extension cables 1546 or contraction cables 1548 to provide force assistance to the wearer. For example, when a pulling force is applied to a lower hinged assembly 1616*b* by extension cables 1546 through the actuators 1630, a torque is applied to the sprocket 1564 (FIG. 15) causing the insole bracket 1566 to be rotated downwards with respect to the upright member 1554 thereby assisting the user in moving their toes downwards (i.e., extension). Conversely, when a pulling force is applied to contraction cables 1548 by actuators 1630, a torque is applied to sprocket 1564 causing the insole bracket 1566 to be rotated upwards with respect to the upright member 1554 thereby assisting the user in moving their toes upwards (i.e., contraction). In this manner, the upright member 1554 and the insole bracket 1566 operate as first and second arms of a hinged connection at the user's joint. The first arm of the hinge (e.g., the upright member 1554) is fixed to the user's limb (e.g. by orthotic cuff 1556 around the lower leg), while the second arm of the hinge (e.g., insole bracket 1566) is positioned along a user's foot. Similarly, the actuators 1630 may assist in extension and contraction of the upper hinged assembly 1616*b* proximate to a user's knee to provide assistance to such joints during various portions of the gait cycle.

The state machine may receive input from one or more sensors 1672, and use current and previous input values in order to determine a current state of the state machine. The current state is then used to determine the timing of the actuator 1630 activation, in order to provide torque assistance to the user with appropriate timing and intensity (e.g., to provide extension assistance during toe-off, or contraction assistance during foot swing to prevent drop foot).

In some embodiments, the feedback modality 1618 provides feedback regarding the individual's use of a wearable exoskeleton device 1610 in a free-living environment. Various types of feedback mechanisms (e.g., auditory, visual, electro-tactile, vibro-tactile) and various locations of placement (e.g., leg, arm, torso, within the control unit 1612 or electronic device 1686) are suited for providing performance tracking during exoskeleton device 1610 assisted walking. In some examples, the feedback modality 1618 may include small vibratory actuators may be used to provide vibro-tactile feedback. Additionally or alternatively, the feedback modality 1618 may include electrical stimulation that may be used to provide electro-tactile feedback. Additionally or alternatively, the feedback modality 1618 may include an LED array or other visual display that may be used to provide color-coded visual feedback. Additionally or alternatively, the feedback modality 1618 may include feedback utilizing one or more of wired or wireless (e.g., Bluetooth) headphones or a small piezo speaker that modulates a beep frequency to provide auditory signals to the individual. Each of the above feedback modalities may be used at logical body placements, which includes possible locations on the leg, hip, torso, and wrist. For example, vibro-tactile and electro-tactile feedback may be suitable for several different locations, while visual feedback may be suitable on locations that are easily seen by the individual user, such as the wrist.

Figure 17:
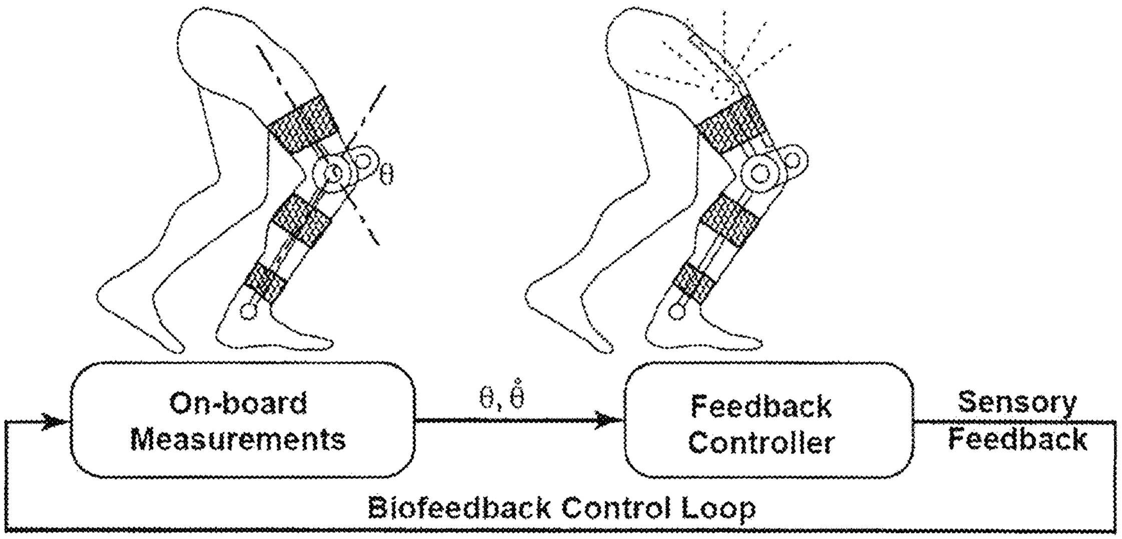
FIG. 17 is a diagram illustrating a knee joint angle that may be measured through the usage of the exoskeleton device, according to some embodiments.

In some embodiments, the controller 1678 may provide instructions to a particular feedback modality 1618 based on the input received from any of the embedded sensors 1672. For example, the torque sensor 1574 (or any other sensor) may be configured to measure an angle θ shown in FIG. 17 during the swing phase of an individual's gait. If the angle θ is not reaching the desired value, then the controller 1678 activates a feedback modality 1618 to inform the individual that they are not complying with the desired performance data point. The feedback modality 1618 could include one or more of the various types of feedback described herein (tactile, visual, and auditory). It should be noted that the feedback loop illustrated in FIG. 17 is exemplary only. Other performance parameters such as ankle (as opposed to knee) angles, foot pressures, or combinations or derivatives of these may be used as the basis for device control and/or user feedback. These schemes will be discussed more fully below.

Additionally, compliance with a desired performance data point may also trigger a feedback modality 1618 to inform the individual that they are indeed in compliance, or, the feedback modality 1618 could inform the individual of both compliance and noncompliance. For example, if, in the above example, the modality contains both green and red light sources, the green light source is illuminated if the angle θ reaches the desired value, and the red light source is illuminated if the angle θ is does not reach the desired value. Electromyography may be used to measure the compliance of specific muscles or muscle groups and relay this information through the feedback modality 1618. Likewise, the feedback modality 1618 may provide a first sound from a speaker or within the control unit 1612 or the feedback modality 1618 when a user is in compliance with the performance data point and a second sound when the user is not in compliance with the performance data point. Additionally, sounds may be generated when other conditions are obtained and/or are not obtained.

The feedback modality may also be used in combination with gamification to enhance the experience of gait rehabilitation and to further engage and incentivize the individual with the feedback process. Non-limiting examples include a scoring system based on collecting points, coins, or other rewards based on rehabilitation progress customized to the individual. The application on the electronic device may be designed to allow the individual to play outside of the rehabilitation setting. The application may also be connected to an individual's physical therapist's (or other advisor's) database or electronic device to report progress or may connect to other systems for using the exoskeleton device in a social or competitive context. For example, in the example illustrated in FIG. 18, the exoskeleton device 1610, the electronic device 1686, and/or the feedback modality 1618 may be communicatively coupled with one or more remote sites such as a remote server 1896 via a network/cloud 1898.

The network/cloud 1898 represents one or more systems by which the exoskeleton device 1610, the electronic device 1686, and/or the feedback modality 1618 may communicate with the remote server 1896. Accordingly, the network/cloud 1898 may be one or more of various wired or wireless communication mechanisms, including any desired combination of wired and/or wireless communication mechanisms and any desired network topology (or topologies when multiple communication mechanisms are utilized). Exemplary communication networks include wireless communication networks (e.g., using Bluetooth, IEEE 802.11, etc.), local area networks (LAN) and/or wide area networks (WAN), including cellular networks, satellite networks, microwave networks, radio frequency networks, the Internet and the Web, which all may provide database communication services and/or cloud computing services.

The Internet is generally a global database communications system that is a hardware and software infrastructure, which provides connectivity between computers. In contrast, the Web is generally one of the services communicated via the Internet. The Web is generally a collection of interconnected documents and other resources, linked by hyperlinks and URLs. In many technical illustrations when the precise location or interrelation of Internet resources are generally illustrated, extended networks such as the Internet are often depicted as a cloud (e.g. 1898 in FIG. 9). The verbal image has been formalized in the newer concept of cloud computing. The National Institute of Standards and Technology (NIST) provides a definition of cloud computing as "a model for enabling convenient, on-demand network access to a shared pool of configurable computing resources (e.g., networks, servers, storage, applications, and services) that can be rapidly provisioned and released with minimal management effort or service provider interaction."

Although the Internet, the Web, and cloud computing are not exactly the same, these terms are generally used interchangeably herein, and they may be referred to collectively as the network/cloud 1898.

The server 1896 may be one or more computer servers, each of which may include at least one processor and at least one memory, the memory storing instructions executable by the processor, including instructions for carrying out various steps and processes. The server 1896 may include or be communicatively coupled to a data store 18100 for storing collected data point as well as instructions for operating the exoskeleton device 1610, the feedback modality 1618, the electronic device 1686, etc. that may be directed to and/or implemented by the exoskeleton device 1610, the electronic device 1686, and/or the feedback modality 1618 with or without intervention from a user and/or the electronic device 1686.

In some examples, the instructions may be inputted through the electronic device 1686 and relayed to the server 1896. Those instructions may be stored in the server 1896 and/or data store 18100. At various predefined periods and/or times, the exoskeleton device 1610 and/or the feedback modality 1618 may communicate with the server 1896 through the network/cloud 1898 to obtain the stored instructions, if any exist. Upon receiving the stored instructions, the exoskeleton device 1610 and/or the feedback modality 1618 may implement the instructions. The server 1896 may additionally store information related to multiple exoskeleton devices 1610 and operate and/or provide instructions to the exoskeleton device 1610, the feedback modality 1618, and the electronic device 1886 in conjunction with the stored information with or without intervention from a user. The information may include performance data point from a wide array of users.

Figure 18:
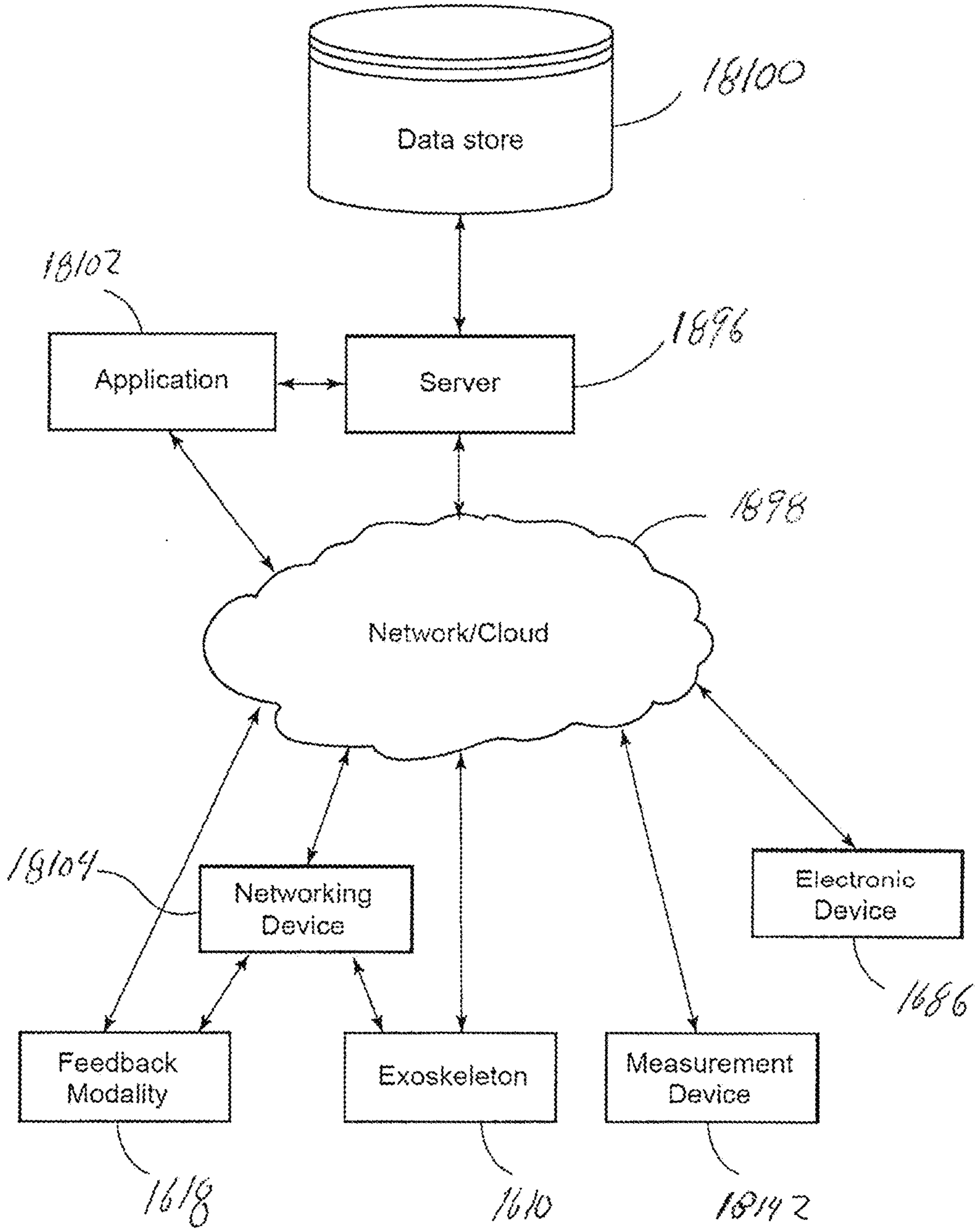
FIG. 18 is a block diagram of the exoskeleton device communicatively coupled with various other devices through a network/cloud, according to some embodiments.

With further reference to FIG. 18, the server 1896 also generally implements features that may enable the exoskeleton device 1610 and/or the feedback modality 1618 to communicate with cloud-based applications 18102. Communications from the exoskeleton device 1610 and/or the feedback modality 1618 can be directed through the network/cloud 1898 to the server 1896 and/or cloud-based applications 18102 with or without a networking device 18104, such as a router and/or modem. Additionally, communications from the cloud-based applications 18102, even though these communications may indicate one of the exoskeleton device 1610 and/or the feedback modality 1618 as an intended recipient, can also be directed to the server 1896. The cloud-based applications 18102 are generally any appropriate services or applications 18102 that are accessible through any part of the network/cloud 1898 and may be capable of interacting with the exoskeleton device 1610 and/or the feedback modality 1618.

In various examples, the electronic device 1686 can be feature-rich with respect to communication capabilities, i.e. have built-in capabilities to access the network/cloud 1898 and any of the cloud-based applications 18102 or can be loaded with, or configured to have, such capabilities. The electronic device 1686 can also access any part of the network/cloud 1898 through wired or wireless access points, cell phone cells, or network nodes. In some examples, users can register to use the remote server 1896 through the electronic device 1686, which may provide access the exoskeleton device 1610 and/or the feedback modality 1618 and/or thereby allow the server 1896 to communicate directly or indirectly with the exoskeleton device 1610 and/or the feedback modality 1618. In various instances, the exoskeleton device 1610 and/or the feedback modality 1618 may also communicate directly, or indirectly, with the electronic device 1686 or one of the cloud-based applications 18102 in addition to communicating with or through the server 1896. According to some examples, the exoskeleton device 1610 and/or the feedback modality 1618 can be preconfigured at the time of manufacture with a communication address (e.g. a URL, an IP address, etc.) for communicating with the server 1896 and may or may not have the ability to upgrade or change or add to the preconfigured communication address.

Referring still to FIG. 18, when a new cloud-based application 18102 is developed and introduced, the server 1896 can be upgraded to be able to receive communications for the new cloud-based application 18102 and to translate communications between the new protocol and the protocol used by the exoskeleton device 1610 and/or the feedback modality 1618. The flexibility, scalability, and upgradeability of current server technology render the task of adding new cloud-based application protocols to the server 1896 relatively quick and easy.

In some examples, wearable assistance system includes the exoskeleton device 1610, the feedback modality 1618, the electronic device 1686, and/or a measurement device 18142. The measurement device is configured to generate biomechanical data points of an individual. The collected data points can then be used to determine an individual's gait deficits. The controller 1678 of the exoskeleton is configured to actuate the actuator 1630 at an initial level of assistance based on the gait deficits. In various examples, the measurement device is a motion capture camera configured to detect movement and force gait analysis. Additionally or alternatively, the measurement device utilizes a measurement of muscle activity through electromyography. Additionally or alternatively, the measurement device utilizes a measurement of oxygen consumption/CO2 production to determine a metabolic rate. The generated biomechanical data point of the individual can be compared to a computer-generated model of a gait cycle.

In some embodiments, the amount of assistance a user may need may increase or decrease over time. For example, as a disease continues, the amount of mobility of a user may decrease, thus, they may need increased assistance. On the other hand, in some situations, with or without the use of the exoskeleton device, a user may be able to improve their mobility or strength, thus, may need less assistance over time. Accordingly, the controller can be configured to decrease the level of assistance or increase resistance when the change in the at least one data point is indicative of increased performance by an individual using the exoskeleton device. Conversely, the controller can be configured to increase the level of assistance or decrease resistance when the change in the at least one data point is indicative of decreased performance by an individual using the exoskeleton device. To account for possible changes in assistance, an exoskeleton device control algorithm capable of establishing and tracking personalized measures of exoskeleton device 1610 assisted walking performance may be present within the control unit 1612 and/or located in the server 1896, which may be accessed through the network/cloud 1898. In the example shown in FIG. 19, a hierarchical control strategy is programmed onto the memory (e.g., 1682 or 18100). As provided herein, the control strategy utilizes data points from one or more sensors 1672 embedded in the exoskeleton device 1610 to track posture and/or other data points, evaluate how these data points change over time and adjust the level of assistance accordingly.

Figure 19:
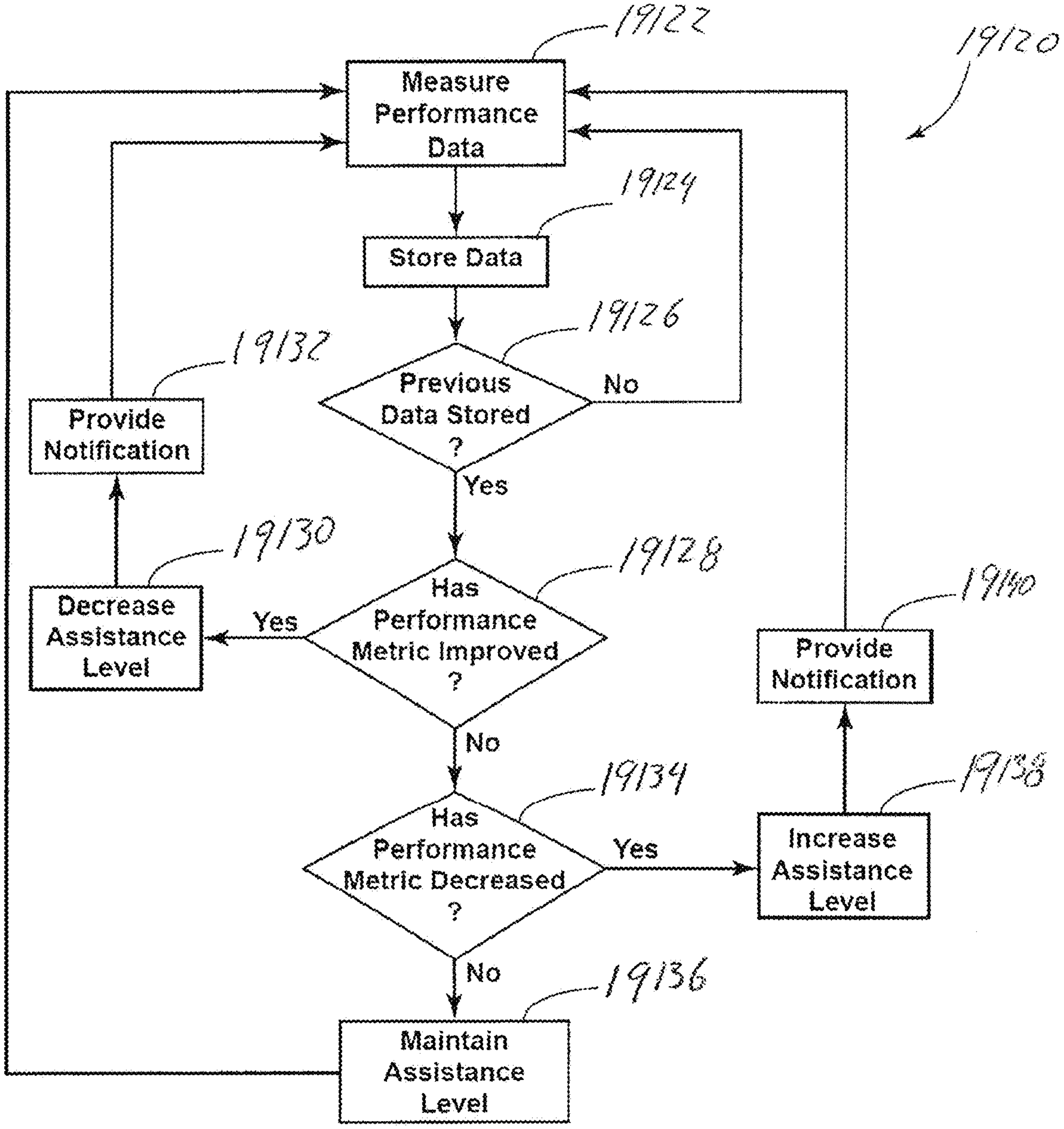
FIG. 19 is a flowchart of a method of dynamically (intermittently) updating a level of assistance provided by the exoskeleton device based on a sensor data point, according to some embodiments.

For example, in the embodiment illustrated in FIG. 19, an example of a closed loop method 19120 for adaptively altering an amount of assistance is provided. In the embodiment illustrated in FIG. 19, the method begins at step 19122, in which a user's performance is measured by the one or more sensors 1672, 1574, 1576, etc. embedded within the exoskeleton device 1610. In various examples, the one or more sensors can be incorporated at the lower hinged assembly 1616*a* (FIG. 16) of the exoskeleton device 1610 to measure the forces being applied to the foot and/or the speed of ankle rotation, at the upper hinged assembly 1616*b* to measure a degree of rotation of the knee through the gait cycle, and/or at the hip to measure the kinematics of the hip joint through the gait cycle. These measurements can be used to determine the stance versus swing phase of the walking motion. Depending on the specific gait deficit of the individual, the exoskeleton device 1610 may include one or more types of sensors 1672 and/or one or more of the same type of sensor 1672.

At step 19124, the measured data point is stored in the memory of the control unit 1612, in the data store 18100 that is remote from the exoskeleton device 1610, and/or in the electronic device 1686. The stored data point may be retained in any manner. The stored data point may be accessed by the control unit 1612 of the exoskeleton device 1610, the feedback modality 1618, and/or a remote electronic device 1686. The remote electronic device 1686 may be accessed by a remote advisor, such as a physical therapist, who can, in turn, monitor the usage of the exoskeleton device 1610 and/or adjust the assistance level provided by the exoskeleton device 1610 remotely. In addition, the electronic device 1686 may also be a database that compiles the stored data point from one or more users that can be used for a wide array of analyses and adjustments in assistance levels.

At step 19126, the method determines if measurement data point regarding a specific user has previously been stored. If no data point has previously been stored, the method returns to step 19122 and measures additional performance data point. If previous data point has been stored, the method continues to step 19128 in which the most recently collected data point is compared to previously obtained data point to determine when a performance metric has increased. To determine a performance metric, any of the data points collected by the exoskeleton device 1610 may be used. In some embodiments, the most recently obtained data point may be compared to a predefined number of previous cycles. For example, the most recent data point may be compared to 100 (or any other number of) previous data point acquisition cycles. The comparisons may be used to define trends, which in turn, may be used to determine a prolonged performance trend of the user. The prolonged performance trend may be used for determining whether to adjust the assistance level of the exoskeleton device 1610.

If the performance metric of the user has increased, the method continues to step 19130 in which the amount of assistance or resistance provided by the exoskeleton device 1610 is adjusted (increased or decreased). In some embodiments, the method continues to step 19132 wherein a notification is provided to the user that their performance has increased by at least a threshold amount, and thus, the amount of assistance provided will be reduced. The method may then continue back to step 19122 to collect the next iteration of data point.

If at step 19128 it is determined that the performance metric hasn't improved by at least a threshold level, the method continues to step 19134, where the method determines whether the performance data point has decreased by a threshold amount. If the performance data point has not decreased by a threshold amount, then the method continues to step 19136 where the amount of assistance or resistance provided is maintained. Next, the method returns to step 19122 where an additional cycle of data point is collected.

If at step 19136 it is determined that the performance metric has fallen below the threshold level, the method continues to step 19138 wherein the amount of assistance provided by the exoskeleton device 1610 is increased. Next, the method can continue to step 19140, where a notification is provided to the user and/or another person that the performance data point has fallen and that additional assistance or resistance will be administered. The method then returns to step 19122 to collect additional data point.

Accordingly, as a non-limiting example of the method, a sensor 1672 may measure the angle θ during the swing phase of an individual's gait. If the angle θ is not reaching the desired value at a certain level of assistance, then the controller 1678 instructs the actuator 1630 to increase assistance. Conversely, if the angle θ is consistently reaching the desired value at a given level of assistance, then the controller 1678 instructs the actuator 1630 to gradually decrease the assistance level. If the performance metric is being met within upper and lower bands, the assistance level provided by the exoskeleton device 1610 may be maintained. Additionally or alternatively, the method can provide the user with positive or negative feedback when the user meets or fails to meet some performance metric, and this feedback may be provided instead of or in addition to decreasing or increasing assistance.

Use of the present disclosure may offer a variety of advantages, which is provided by various combinations of the features provided herein. For example, the exoskeleton device provided herein may provide assistance to any number of joints of a user. Moreover, the assistance or resistance may be provided in a real-world environment, versus just in a lab. The exoskeleton may be minimally invasive to the user during day-to-day activities and manufactured at substantially reduced costs compared to various other assistance devices that are commercially available. The exoskeleton may provide assistance during some modes of operation specifically intended to improve mobility or posture. Additionally or alternatively, the exoskeleton may provide resistance a mode of operation designed to increase muscle recruitment during a function task (e.g. walking). The exoskeleton provided herein may be coupled with a feedback modality that allows for feedback regarding use of the exoskeleton device. For example, the user modality may alert a user when various performance goals are met. In addition, the exoskeleton may be remotes coupled to an electronic device. The electronic device may obtain data regarding the exoskeleton device and/or provided controls for altering usage of the exoskeleton device. In addition, the exoskeleton device may include one or more algorithms for intermittently adjusting the assistance level of the exoskeleton device based on the user performance. The assistance level may be changed from an initial assistance level that is obtained through various methods provided herein that make it quicker and more obtainable for a user with gait deficits to be fitted with the exoskeleton device.

Experience with use of various performance metrics and feedback methodologies has allowed Applicants to expand and improve on the systems and methods thus far described. In particular, in practice, Applicants have determined that direct measurements of ankle torque and measurements of pressure sensors placed beneath the footbed or insole bracket of an ankle orthosis described above may produce inaccurate or otherwise disadvantageous datapoints for use in determining whether a user is walking in accordance with the user's treatment program or otherwise correctly.

Applicants have determined that the point in the gait cycle at which a person develops peak ankle power is a useful performance metric in determine whether someone is walking with a normal gait. Thus, both the timing (within the stance phase) and the magnitude of peak ankle power (i.e., relative to historical peak ankle power for the user or relative to averages determined from normal walkers) are useful performance metrics with which to perform gait training, i.e., providing feedback to encourage people to walk with a normal gait. A person with a normal gait will generally develop peak ankle power near the end of the stance phase of the gait, which is the point at which a person is most forcefully driving the ball of the foot into the ground prior to pushoff and swing. Thus, one goal of gait training should be to encourage a person undergoing treatment to be developing maximal ankle power, or power at or above some predetermined level, just prior to pushoff.

It was previously believed that foot pressure measured a pressure sensor located in the footbed of an orthosis such as those described here (e.g., the sensor 1576 in FIG. 15 located under the forefoot) could be used to provide an estimate (or at least a relative indication) of ankle power, and thus could be used as the basis for feedback training. According to this method, forefoot pressure sensor readings would be taken for a user wearing a device such as those described above including a forefoot pressure sensor and peak pressure values were recorded. An average peak pressure value was computed on the basis of these measurements. This average value was normalized to "1". After this calibration procedure, which might occur periodically or continuously during device use on a rolling basis, forefoot pressure was measured as a user of the device walked. The measured values where then normalized by the average computed during the calibration cycle, and the resulting normalized measured value was compared to the calibrated value (i.e., "1"). In cases where the user failed to maintain the average peak pressure, or if the measured pressure was outside of some range below the average peak pressure, negative feedback indicating such was provided (e.g., a red light, or a first type of sound). In cases where the measured pressure was at, above, or within some range above the average peak pressure value, positive feedback was provided (e.g., a green light, or a second type of sound).

It was discovered, unexpectedly, that this method of gait training produced poor results. In practice, users learned to game or cheat the system by artificially loading their forefoot during the stance phase to guarantee positive feedback. Users would do this, for example, by "bouncing" on their forefoot prior to pushoff. This allowed them to proceed through pushoff with lower than optimal ankle power without triggering the negative feedback mechanism.

Figure 20:
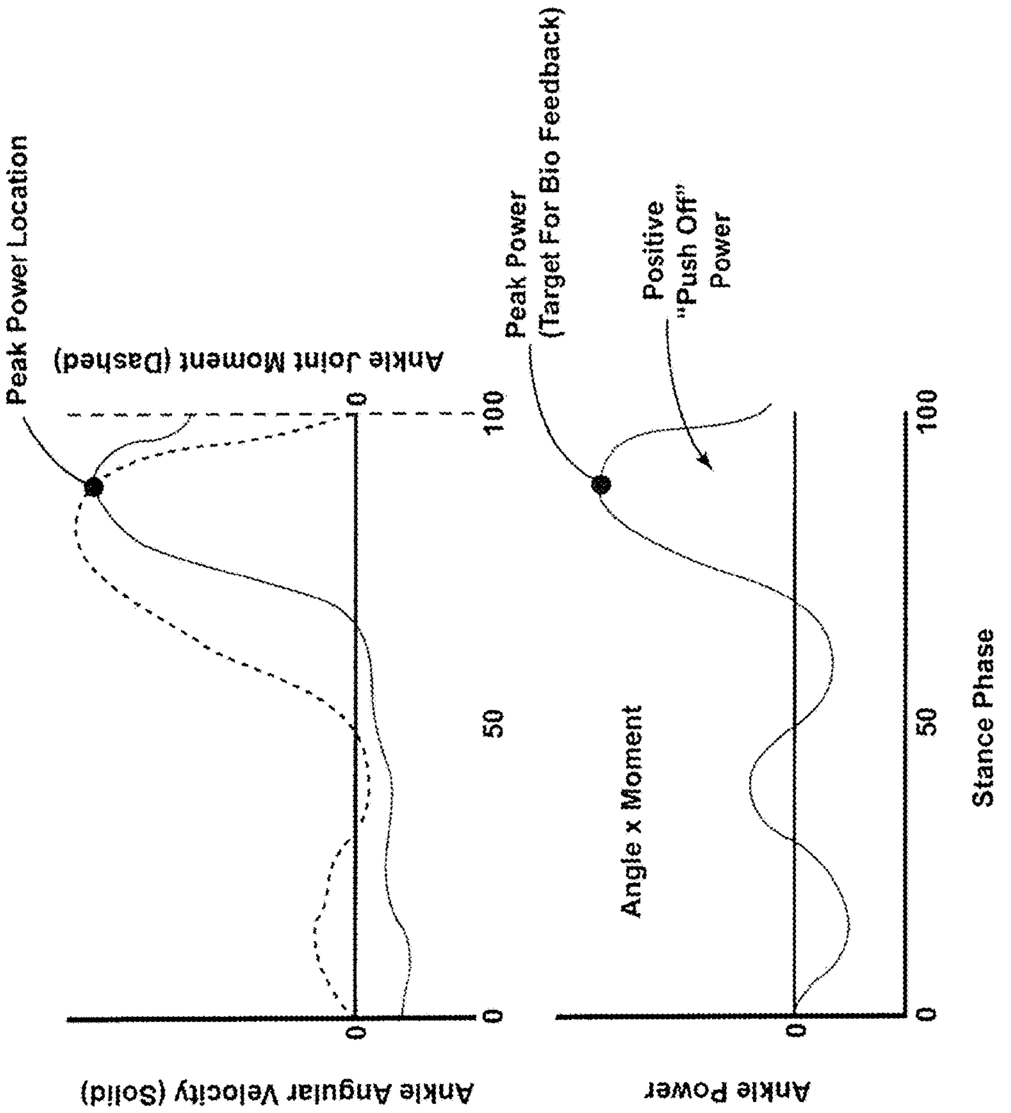
FIG. 20 is a sketch showing the relationship between joint moment, angle velocity and joint power.

Disclosed herein is an improved method for providing gait training with an ankle orthosis based on an improved estimate of peak ankle power. The lower pane of FIG. 20 shows, for a normal gait, a plot of ankle power throughout the stance phase of the gait, where positive ankle power reflects power applied in the direction of extension of the foot. In late stance, peak power is developed during pushoff, as the ankle is driving the forefoot into the ground and the heel is rotating up off the ground. Ankle power drops to zero just as the foot leaves the ground and enters stance phase.

Applicants have determined that the point of peak ankle power in a correct gait can be estimated as the product of ankle joint moment and ankle angle velocity. This is illustrated in the upper pane of FIG. 20. Ankle joint moment may be accurately estimated from the forefoot pressure sensor reading and knowledge of the geometry of the orthosis (i.e., the distance along the footbed from its point of intersection with an axis parallel to the shank that intersects the center of the bearing). That said, an estimate of absolute ankle joint moment is not necessary to provide user feedback on the basis of predetermined target metrics based on use of the same orthosis. Relative ankle joint moment (i.e., relative to previous uses or average uses of the same device) may be determined just be measurements taken with the pressure sensor. Additionally, by measuring both pressure under the forefoot and ankle angular velocity, and computing and tracking the product of those quantities over the gait cycle, a peak value may be determined obtained, which occurs at or near the point at which peak ankle power is developed during push off.

In reliance on this observation, improved methods of providing feedback to a user of an ankle orthosis are provided. According to these methods, ankle velocity is measured with an angle sensor, which may be located proximate to the ankle bearing in any of the devices described above (e.g., joint angle encoder 1574 in the FIG. 15 embodiment). Additionally, ankle moment (or relative ankle moment) is estimated by a pressure sensor located under the forefoot of the device (e.g., 1576 in FIG. 15). The pressure sensor may be, for example, a force sensitive resistor. These two values are measured periodically or continuously during a user's gait and are multiplied together (preferably after scaling or normalization one or both raw measurements) to provide an estimate of ankle power. The point at which product is highest is an estimate of peak ankle power, which may be used as a performance metric. This performance metric may then be used like any of the uses of performance metrics described above. In particular, it may be compared to a predetermined value, before or after scaling or normalization, to determine whether the user's performance matches or is within some range of acceptable performance.

The disclosed method includes an angle sensor (e.g., potentiometer) or angle encoder (e.g., an optical angle encoder or Hall-effect angle encoder) to measure ankle angular velocity at or near the rotational bearing. However, other techniques and arrangements for measuring ankle angular velocity are possible and within the scope of the invention. For example, ankle angular velocity may be determined by any collection and arrangement sensors capable of measuring the position of the footbed relative to the shank over time. With data showing how the footbed is moving relative to the shank, e.g., from any positional sensors capable of gathering this information, and with knowledge of how the orthosis is constructed (i.e., the position of sensors on the footplate and/or shank relative to the axis of rotation) the angular position of the footbed relative to the shank over time can be determined and the ankle angular velocity can be calculated. For example, a simple pair of sensors (e.g., magnetic position sensors) capable of determining the distance between the sensors over time could be used to determine ankle angular velocity if one were located on the shank and one were located on the footbed at known distances from the axis of rotation (that is, the center of the bearing). In other embodiments, one or more inertial measurement units (IMUs) are used on one of the shank or the footplate to measure the direction and magnitude of inertial changes of both parts. With a calibration procedure, these inertial data may be used to determine ankle angular velocity. Thus, as used herein, an angle sensor or ankle angle sensor may include not only an angle encoder, but any sensor or combination of sensors arranged and capable of measuring the angle between the footplate and the shank over time.

In one embodiment, peak ankle power (or relative peak ankle power) is estimated according to the method set forth above for a number of steps over time (e.g., 100). Those values may then be averaged to generate an average peak ankle power estimate. Multiple average peak ankle power values may be determined for various walking speeds. Peak ankle power can later be estimated according to the disclosed method during use of the device (e.g., during free use, but preferably during a physical therapy session), and the measured value compared to the average value. If the measured estimates are below the average value, or below some predetermined range below the average value, the user can be given a first feedback (e.g., a red light, a negative or unpleasant sound or a first vibrotactile feedback, or some combination of the foregoing). Alternatively or additionally, assistance or resistance can increased or decreased (i.e., to encourage the user to develop more peak ankle power on their own). If the measured estimates are at, or within some range of or above the average peak power value, the user can be provided with a second feedback (e.g., a green light, a pleasant sound or a second vibrotactile feedback or some combination of the foregoing), and again, assistance or resistance can be increased or decreased. As part of this process, the average peak ankle power measurement can be scaled up or down to set aspirational performance goals to encourage the user to meet different performance targets.

It will be appreciated that by estimating ankle power as a product of ankle velocity and ankle moment, it is much more difficult for the user to game or cheat the disclosed gait training method. If the user artificially loads the user's foot early in the gait cycle, while ankle angle velocity is low, the user will not generate a high ankle power measurement according to this method. By computing a product of both pressure and ankle angular velocity, and by providing biofeedback on that parameter, the method ensures that user must provide high pressure at or near the moment of high ankle angular velocity. Thus, an ankle power performance metric computed according to this method encodes both magnitude and timing information, and provides a feedback tool as a simple, one-number parameter that is especially useful for gate training.

It will be further appreciated that the gait training method described herein may be used on any of the devices described above, including both active devices, passive devices, and combinations of the two. Indeed, while it is contemplated that this feedback/training methodology may be used in connection with orthoses designed to provide active or passive assistance or resistance (i.e., with pulleys and cables, leaf springs, variable tensioned leaf springs, or combinations of these), this is not a requirement. The disclosed gait training methodology may also be used on entirely non-assistive devices to help train gait. For example, a completely passive and non-assistive brace could be provided that lacks any assistive features at all. Such a brace would include, for example, a vertical shank 1554, a cuff and associated straps for securing the shank to the leg (1556, 1558, 1560), a rotational bearing located at the angle (1562) that rotationally coupled a footbed 1566 to the shank, all in the manner depicted in FIG. 15. An angle encoder would be provided in the bearing to measure the angle between the footbed and shank over time, and a pressure sensor under the forefoot (below or on top of) the footbed would be provided. Such a device would be completely passive, lacking any ability to provide rotational assistance to the footbed. However, such a completely passive and non-assistive device could be used for rehabilitation and gait training in the manner described above. Such a device might be useful when a patient was nearing the very end of the patient's course of rehabilitation and needed only a small amount of reinforcement to walk normally, or if the patient was experiencing only a modest degree of gait abnormality that could be corrected with training and feedback, but without resistance or assistance.

The exemplary embodiments described above have been AFO's or orthoses that provide assistance or resistance to a user's ankle. The personal of ordinary skill will appreciate that the teachings of this disclosure are equally applicable to other joint orthoses such as orthoses for wrists, knees and elbows.

It will be understood by one having ordinary skill in the art that construction of the described invention and other components is not limited to any specific material. Other exemplary examples of the invention disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

Furthermore, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected" or "operably coupled" to each other to achieve the desired functionality, and any two components capable of being so associated can also be viewed as being "operably couplable" to each other to achieve the desired functionality. Some examples of operably couplable include, but are not limited to, physically mateable, physically interacting components, wirelessly interactable, wirelessly interacting components, logically interacting, and/or logically interactable components.

It is also important to note that the construction and arrangement of the elements of the invention as shown in the examples are illustrative only. Although only a few examples of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system might be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary examples without departing from the spirit of the present innovations.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment.

The exemplary structures disclosed herein are for illustrative purposes and are not to be construed as limiting. In addition, variations and modifications can be made on the aforementioned structures without departing from the concepts of the present invention and such concepts are intended to be covered by the following claims unless these claims by their language expressly state otherwise.

The invention claimed is:

1. An exoskeleton device, comprising:

a shank and a footplate rotatably coupled to the shank via a rotational bearing;

an angle sensor configured to measure an angle between the shank and the footplate and the velocity of the angular change between the shank and the footplate;

a pressure sensor at the footplate configured to measure pressure exerted by a user's foot;

a feedback modality; and a controller including a microprocessor in communication with the angle sensor and the pressure sensor, the controller configured to compute an estimate of joint ankle power developed by the user during stance phase while walking, and to activate the feedback modality based on a comparison of the estimate of peak joint ankle power and a predetermined metric; wherein the controller is configured to compute the estimate of joint ankle power by estimating peak joint ankle power by measuring a series of products of user ankle angular velocity and user foot pressure taken during stance phase while the user walks and selecting a peak product of the series of products.

2. The device of claim 1, wherein computing the estimate of joint ankle power comprises computing a series of products of measurements of user ankle angular velocity and user foot pressure taken during stance phase while the user walks and computing the average of the products or integrating across the products.

3. The device of claim 1, further comprising a transceiver configured to wirelessly transmit sensor data to the controller, and wherein the controller is located in a computing device remote from the shank and footplate.

4. The device of claim 1, wherein the controller activates the feedback modality in a first state to indicate compliance with the performance metric and a second state to indicate non-compliance with the performance metric.

5. The device of claim 1, wherein the performance metric is based on an average of historical peak products of measurements taken by the angle and pressure sensors during stance phase while the user walks.

6. The device of claim 1, wherein the feedback modality is housed in a device remote from shank and footplate.

7. The device of claim 1, wherein the feedback modality comprises an LED array configured to provide color-coded visual feedback.

8. The device of claim 1, wherein the feedback modality is configured as a speaker.

9. The device of claim 1, wherein the feedback modality comprises a vibrotactile interface that is positioned to supply vibrotactile feedback to the calf of a user of the device.

10. The device of claim 1, wherein the feedback modality is configured as a visual display on a handheld device.

11. The device of claim 1, wherein the feedback modality is configured as a speaker on a handheld device.

12. The device of claim 1, wherein the device further comprises a control unit having at least one actuator and a transmission assembly operably coupling the actuator to the hinged assembly and configured to rotate the footplate with respect to the shank.

13. The device of claim 12, wherein the controller is configured to cause the actuator to rotate the footplate with respect to the shank based on the comparison of the estimate of peak joint ankle power and a predetermined metric.

14. The device of claim 13, wherein the controller is configured to rotate the footplate in a direction of foot extension based on non-compliance with the performance metric.

15. The device of claim 1, wherein the sensors are in electronic communication with the controller via a wireless transceiver, and wherein the controller including the microprocessor is housed in one of a smart phone, tablet or personal computer.

16. The device of claim 15, wherein the controller including the microprocessor is housed in a portable electronic device, which is configured to provide the feedback modality.

17. The device of claim 1, wherein the controller including the microprocessor is housed proximate to the shank and hinged assembly.

18. The device of claim 1, wherein the feedback modality is configured as a scoring system based on collecting rewards based on repeated compliance with the performance metric.

19. The device of claim 1, further comprising a carbon fiber leaf spring configured to provide adjustable assistance or resistance to the user's ankle plantar flexion or dorsi flexion during walking.

20. The device of claim 1, wherein the transmission assembly comprises a pair of Bowden cables and a pulley coupled to the bearing.

21. The device of claim 1, wherein the angle sensor is one of an angle encoder, an inertial measurement unit and an array of positional sensors.

* * * * *